(12) United States Patent
Merzaban et al.

(10) Patent No.: US 11,892,446 B2
(45) Date of Patent: Feb. 6, 2024

(54) FLUORESCENT MULTIPLEX CELL FLOW SYSTEMS AND METHODS

(71) Applicant: King Abdullah University of Science and Technology, Thuwal (SA)

(72) Inventors: Jasmeen Merzaban, Thuwal (SA); Ayman F. Abuelela, Thuwal (SA); Amal J. Ali, Thuwal (SA)

(73) Assignee: KING ABDULLAH UNIVERSITY OF SCIENCE AND TECHNOLOGY, Thuwal (SA)

( * ) Notice: Subject to any disclaimer, the term of this patent is extended or adjusted under 35 U.S.C. 154(b) by 890 days.

(21) Appl. No.: 15/774,648

(22) PCT Filed: Nov. 28, 2016

(86) PCT No.: PCT/IB2016/001764
§ 371 (c)(1),
(2) Date: May 9, 2018

(87) PCT Pub. No.: WO2017/089888
PCT Pub. Date: Jun. 1, 2017

(65) Prior Publication Data
US 2021/0311021 A1    Oct. 7, 2021

Related U.S. Application Data

(60) Provisional application No. 62/260,557, filed on Nov. 29, 2015.

(51) Int. Cl.
| | | |
|---|---|---|
| *G01N 33/50* | (2006.01) | |
| *G01N 15/14* | (2006.01) | |
| *G01N 21/05* | (2006.01) | |
| *G01N 21/64* | (2006.01) | |
| G01N 15/10 | (2006.01) | |

(52) U.S. Cl.
CPC ..... *G01N 33/5029* (2013.01); *G01N 15/1436* (2013.01); *G01N 15/1459* (2013.01); *G01N 15/1484* (2013.01); *G01N 21/05* (2013.01); *G01N 21/645* (2013.01); *G01N 21/6486* (2013.01); *G01N 33/5073* (2013.01); *G01N 2015/1006* (2013.01)

(58) Field of Classification Search
CPC . G01N 15/1436; G01N 33/5029; G01N 21/05
See application file for complete search history.

(56) References Cited

U.S. PATENT DOCUMENTS

| | | |
|---|---|---|
| 2011/0086363 A1 | 4/2011 | Mutus |
| 2014/0274739 A1 | 9/2014 | Rinker |

FOREIGN PATENT DOCUMENTS

| | | |
|---|---|---|
| EP | 2818244 | 12/2014 |
| WO | 2013086284 | 6/2013 |

OTHER PUBLICATIONS

Sukhdeo et al., PLOS One, 20138(1) e53015, p. 1-9.*
Brown, et al., "Improvements to parallel plate flow chambers to reduce reagent and cellular requirements", BMC Immunology, 2:9 (2001).
International Search Report for corresponding PCT application PCT/IB2016/001764 dated Mar. 13, 2017.
Lawrence, et al., "Effect of flow on polymorphonuclear leukocyte/endothelial cell adhesion", Blood, 70(5):1284-1290 (1987).
Sperandio, et al., "Analysis of leukocyte rolling in vivo and in vitro.", Methods in Enzymology, 416:346-371 (2006).

* cited by examiner

*Primary Examiner* — Bin Shen
(74) *Attorney, Agent, or Firm* — PABST PATENT GROUP LLP

(57) ABSTRACT

Systems and methods are provided for simultaneously assaying cell adhesion or cell rolling for multiple cell specimens. One embodiment provides a system for assaying adhesion or cell rolling of multiple cell specimens that includes a confocal imaging system containing a parallel plate flow chamber, a pump in fluid communication with the parallel plate flow chamber via a flow chamber inlet line and a cell suspension in fluid communication with the parallel plate flow chamber via a flow chamber outlet line. The system also includes a laser scanning system in electronic communication with the confocal imaging system, and a computer in communication with the confocal imaging system and laser scanning system. In certain embodiments, the laser scanning system emits multiple electromagnetic wavelengths simultaneously it cause multiple fluorescent labels having different excitation wavelength maximums to fluoresce. The system can simultaneously capture real-time fluorescence images from at least seven cell specimens in the parallel plate flow chamber.

12 Claims, 23 Drawing Sheets

FLUORESCENT MULTIPLEX CELL FLOW SYSTEMS AND METHODS

CROSS-REFERENCE TO RELATED APPLICATIONS

This application claims priority to U.S. Provisional Application No. 62/260,557 entitled "Fluorescent Multiplex Cell Flow Systems and Methods" filed Nov. 29, 2015, the contents of which is incorporated by reference in its entirety.

FIELD OF THE INVENTION

The invention is generally directed to systems and methods for investigating cell rolling and cell-cell adhesion, in particular systems and methods incorporating parallel plate flow chambers.

BACKGROUND OF THE INVENTION

A major challenge for cell-based therapy is the inability to systemically target a large quantity of viable cells with high efficiency to tissues of interest following intravenous introduction. Consequently, increasing cell homing is currently studied as a strategy to improve cell therapy. Cell rolling and cell-cell adhesion on the vascular endothelium is an important step in the process of cell homing and can be probed in vitro using a parallel plate flow chamber assay (Lawrence, M. B., et al., Blood, 70(5):1284-1290 (1987); Brown, D. C., et al., BMC Immunology, 2:9 (2001); Sperandio, M., et al., Methods in Enzymology, 416:346-371 (2006)). However, this is an extremely tedious, low throughput assay. With the need to study multiple samples and multiple ligands, using this light microscope-based flow assay allows only one sample at a time which brings about high inter-experiment variability, requirement for normalization, waste of materials and is significantly time consuming.

Therefore it is an object of the invention to provide parallel plate flow chamber systems and methods for processing multiple samples simultaneously.

It is another object of the invention to provide parallel plate flow systems and methods with higher throughput capacity than conventional systems.

It is still another object of the invention to provide parallel plate flow systems and methods that allow for the analysis of multiple adhesion events in real-time.

It is yet another object of the invention to provide parallel plate flow systems and methods for improving cell-based therapies.

SUMMARY OF THE INVENTION

Systems and methods are provided for simultaneously assaying cell adhesion or cell rolling for multiple cell specimens. One embodiment provides a system for assaying adhesion or cell rolling of multiple cell specimens that includes a confocal imaging system containing a parallel plate flow chamber, a pump in fluid communication with the parallel plate flow chamber via a flow chamber inlet line and a cell suspension in fluid communication with the parallel plate flow chamber via a flow chamber outlet line. The system also includes a laser scanning system in electronic communication with the confocal imaging system, and a computer in communication with the confocal imaging system and laser scanning system. In certain embodiments, the laser scanning system emits multiple electromagnetic wavelengths simultaneously it cause multiple fluorescent labels having different excitation wavelength maximums to fluoresce. The system can simultaneously capture real-time fluorescence images from at least seven cell specimens in the parallel plate flow chamber.

Another embodiment provides a method for assaying cell adhesion or cell rolling of multiple cell specimens by contacting each cell specimen with a primary binding agent that specifically binds to an epitope on cells of the cell specimen. The method includes contacting each cell specimen with a second binding agent conjugated to a fluorescent label, wherein each cell specimen is contacted with a second binding agent comprising a different fluorescent label and the second binding agent specifically binds to the primary agent in the cell specimen. After contacting the cell specimens with the binding agents, the cell specimens are passed through a parallel plate flow chamber and exposed to an amount of electromagnetic energy effective to cause the fluorescent labels to fluoresce. The method also includes capturing real-time fluorescence images of the multiple cell specimens as the multiple cell specimens pass through the parallel plate flow chamber.

Preferred fluorescent labels are selected from the group consisting of Alexa Fluor 405, Alexa Fluor 546, and Alexa Fluor 680. The cells are typically selected from the group consisting of adult stem cells, embryonic stem cells, and induced pluripotent stem cells. Preferred cells are human cells.

One embodiment uses a three-color fluorescence staining approach, which allows eight different combinations of fluorescent cell identities to be run in a flow experiment at one time. For instance, each cell type or treatment condition can be labeled with a unique fluorescent identity comprised of Alexa Fluor® 405-, Alexa Fluor® 546- or Alexa Fluor® 680-conjugated antibody or combinations thereof. Real-time images are then acquired in a single pass using line-scanning spectral confocal microscope at one frame per 400-millisecond rate. This technique allows for the analysis of adhesion events from up to eight different treatment conditions simultaneously in real-time and to calculate differences in rolling frequency, velocity and tethering capability of cells under study. This assay allows for analysis of rolling cell populations on an endothelial cell layer where populations are competing for occupancy of available sites of interactions in a real-time scenario much like what occurs in vivo. Better understanding of the rolling process for candidate cell types, such as therapeutic stem cells, may lead to development of techniques to enhance cell homing and contribute significantly towards improving cell-based therapy.

By developing methods to better understand cell migration in general, treatments can be envisioned that direct the migration of therapeutic cells, such as stem cells, to specific locations throughout the body but also to inhibit metastasis of detrimental cells such as circulating tumor cells.

Using such assays to measure the rolling process for candidate cell types can lead to development of techniques to enhance cell homing and contribute significantly towards improving cell-based therapy or techniques to inhibit tumor spreading and cancer mortality. Importantly, this technology described here allows for multiple conditions to be tested with improved throughput, permitting rapid and efficient study of rolling properties. Other assays relevant for cell homing, such as cell adhesion, chemotaxis and transmigration, may also be studied with this assay. Overall, this high throughput approach to following the flow of cells over an endothelial monolayer emerges as a powerful technique to study cell rolling and will become a useful tool to aid in the clinical translation of exogenous cell-based therapies.

BRIEF DESCRIPTION OF THE DRAWINGS

In FIG. 5A the columns are from left to right: Control and CD44$^{low}$; CD162$^{low}$, and CD43$^{low}$, CD44$^{low}$/CD162$^{low}$ and CD44$^{low}$/CD43$^{low}$, Tiple KD at the indicated shear stress (dynes/cm$^2$).

DETAILED DESCRIPTION OF THE INVENTION

I. Definitions

Figure 1:
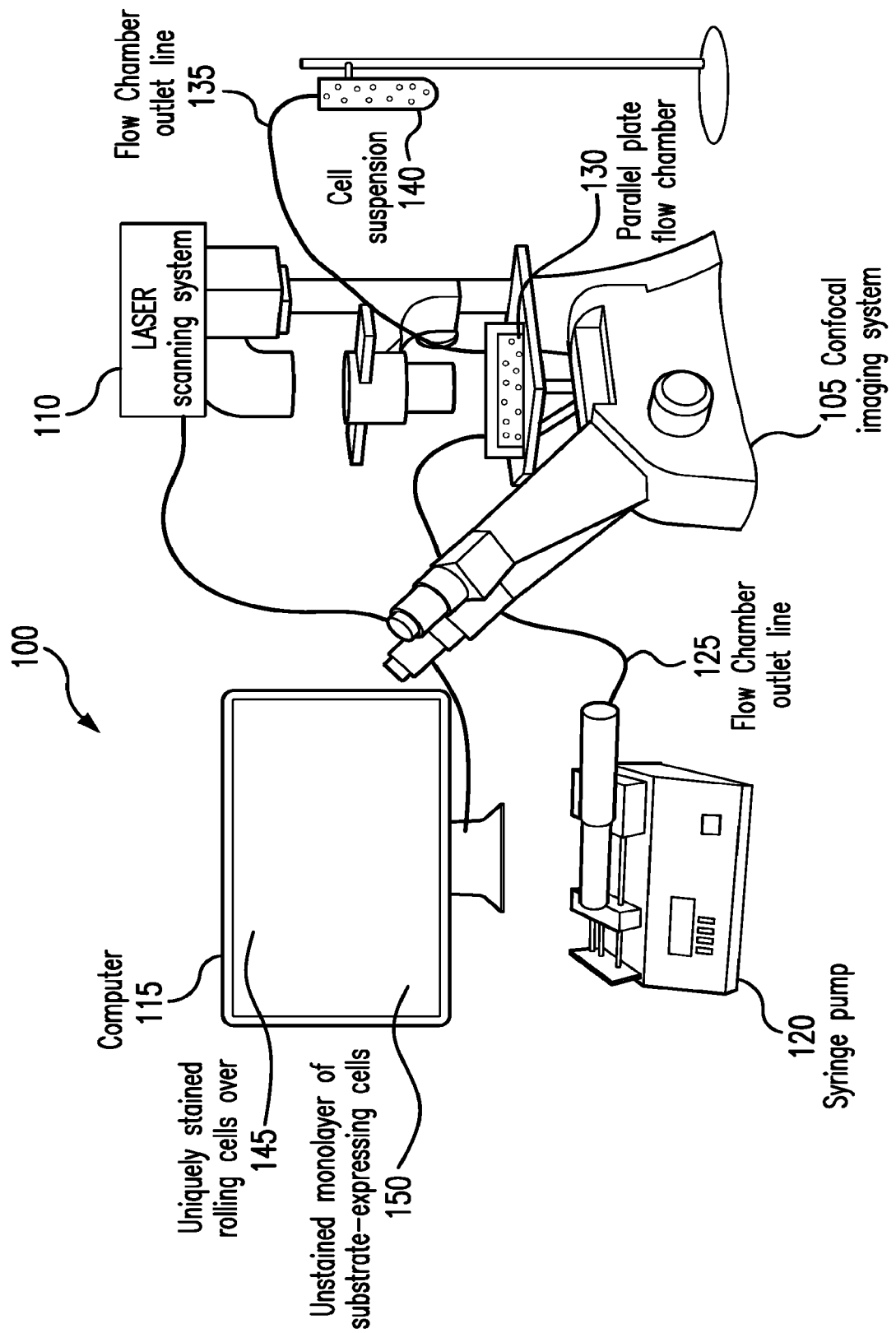
FIG. 1 is an exemplary parallel plate cell flow setup for Fluorescent Multiplex Cell Flow (FMCF).

The use of the terms "a," "an," "the," and similar referents in the context of describing the presently claimed invention (especially in the context of the claims) are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein.

Use of the term "about" is intended to describe values either above or below the stated value in a range of approx. +/−10%; in other embodiments the values may range in value either above or below the stated value in a range of approx. +/−5%; in other embodiments the values may range in value either above or below the stated value in a range of approx. +/−2%; in other embodiments the values may range in value either above or below the stated value in a range of approx. +/−1%. The preceding ranges are intended to be made clear by context, and no further limitation is implied. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The term "cell adhesion molecule" as used herein, generally refers to proteins located on cell surfaces involved in binding (via cell adhesion) of the cell on which it is found with other cells or with the extracellular matrix. Examples of cell adhesion molecules include, but are not limited to, full-length, fragments of, analogs of, and/or modifications of selectins (e.g., E-selectins, P-selectins, L-selectins, etc.), integrins (e.g., ITGA4, etc.), cadherins (e.g., E-cadherins, N-cadherins, P-cadherins, etc.), immunoglobulin cell adhesion molecules, neural cell adhesion molecules, intracellular adhesion molecules, vascular cell adhesion molecules, platelet-endothelial cell adhesion molecules, L1 cell adhesion molecules, and extracellular matrix cell adhesion molecules (e.g., vitronectins, fibronectins, laminins, etc.). As used herein, the term "cell adhesion molecule" also encompasses other compounds that can facilitate cell adhesion due to their adhesive properties. In some embodiments of the invention, aptamers, carbohydrates, peptides (e.g., RGD (arginine-glycine-aspartate) peptides, etc.), and/or folic acid, etc. can serve as cell adhesion molecules. As used herein, such compounds are encompassed by the term "cell adhesion molecule." As used herein, terms referring to cell adhesion molecules including, but not limited to, "cell adhesion molecule," "selectin," "integrin," "cadherin," "immunoglobulin cell adhesion molecule," "neural cell adhesion molecules," "intracellular adhesion molecules," "vascular cell adhesion molecules," "platelet-endothelial cell adhesion molecules," "L1 cell adhesion molecules," "extracellular matrix cell adhesion molecules," encompass full length versions of such proteins as well as functional fragments, analogs, and modifications thereof, unless otherwise stated. Likewise, terms referring to specific cell adhesion molecules including, but not limited to, "E-selectin," "P-selectin," "L-selectin," "ITGA4," "E-cadherin," "N-cadherin," "P-cadherin," "vitronectin," "fibronectin," "laminin," etc., also encompass full length versions of such proteins as well as functional fragments, analogs, and modifications thereof, unless otherwise stated. As used herein, the term "cell adhesion molecule" does not encompass antibodies.

II. The Fluorescent Multiplex Cell Flow (FMCF) System

The disclosed systems and methods incorporate a multiplexing technique that uses unique fluorescent cell labeling (unique Fluorescent identifier) to identify cells within a mixture of differentially labeled cells. The multiplexing technique allows for the analysis of adhesion events from up to eight different treatment conditions simultaneously in real-time. The system provides a competitive setting in which rolling cell populations compete on an endothelial cell layer for occupancy of available sites of interactions mimicking the physiological conditions. The system evades inter-experimental variations and the need for normalization. Additionally the system allows for internal replication by permitting the use of replicates in the same flow run.

One embodiment provides an exemplary system 100 for Fluorescent Multiplex Cell Flow shown in FIG. 1. System 100 includes a confocal imaging system 105 coupled to a laser scanning system 110. The confocal imaging system 105 and laser scanning system 110, for example a Zeiss LSM 710 which is a laser scanning confocal microscope, are in communication with a computer 115. Typically, the imaging system 105 and scanning system 110 are hard wired to the computer 115. However, it will be appreciated that computer 115 can be in wireless communication with system 100 and/or components of system 100.

System 100 is based on the parallel plate flow chamber set-up and can be used to capture adhesive events between flowing cells and endothelial cells in real time. System 100 can be used to visualize tethering and rolling (mediated by the selectins and their ligands) and firm adhesion (mediated by integrins and chemokines) of flowing cells on substrate-expressing cells (i.e., endothelial cells). System 100 includes a suspension of flowing cells 140 in a parallel plate flow chamber 130 connected via soft tubing 135 of the flow chamber inlet line to the parallel plate flow chamber 130. Flowing cells are moving over a monolayer of substrate-expressing cells under fixed sheer stress brought up by controlling the flow rate using a syringe pump 120 in addition to the thickness of flow chamber rubber gasket (not shown). The flow experiment is imaged using a spectral confocal laser scanning system 110 connected to a computer 115

Images are shown on a display component of computer 115. For example, uniquely stained rolling cells 145 and unstained monolayer of substrate expressing cells 150 can be visualized.

Laser scanning system 110 is used to provide electromagnetic energy to excite the fluorophores used to label live cells, preferably mammalian cells, most preferably human cells. Color signatures are detected using simultaneous excitation with multiple excitation laser lines. For example, depending on the fluorophores used, the excitation laser lines can be 488 nm, 561 nm, and 633 nm). In a preferred embodiment the excitation laser line do not intersect.

A. Computer Component

Computer 115 typically contains storage space, memory, one or more processors, and one or more input/output devices such as confocal imaging system 105 and laser scanning system 110. It is to be appreciated that the term "processor" as used herein is intended to include any processing device, such as, for example, one that includes a CPU (central processing unit). The term "memory" as used herein is intended to include memory associated with a processor or CPU, such as, for example, RAM, ROM, etc. In addition, the term "input/output devices" or "I/O devices" as used herein is intended to include, for example, one or more input devices, e.g., keyboard, for making queries and/or inputting data to the processing unit, and/or one or more output devices, e.g., a display and/or printer, for presenting query results and/or other results associated with the processing unit. An I/O device might also be a connection to the network where queries are received from and results are directed to one or more client computers. It is also to be understood that the term "processor" may refer to more than one processing device and that various elements associated with a processing device may be shared by other processing devices. Accordingly, software components including instructions or code for performing the disclosed Florescent Multiplex Cell Flow techniques, as described herein, may be stored in one or more of the associated memory or storage devices (e.g., ROM, fixed or removable memory) and, when ready to be utilized, loaded in part or in whole into memory (e.g., into RAM) and executed by a CPU. The storage may be further utilized for storing program codes, databases of genomic sequences, etc. The storage can be any suitable form of computer storage including traditional hard-disk drives, solid-state drives, or ultrafast disk arrays. In some embodiments the storage includes network-attached storage that may be operatively connected to multiple similar computer servers that comprise a computing cluster.

In a preferred set of embodiments the computer receives input submitted through a graphical user interface (GUI). The GUI may be presented on an attached monitor or display and may accept input through a touch screen, attached mouse or pointing device, or from an attached keyboard. In some embodiments the GUI will be communicated across a network using an accepted standard to be rendered on a monitor or display attached to a client computer and capable of accepting input from one or more input devices attached to the client computer.

B. Flow Chamber

Parallel plate flow chambers are known in the art. See for example Brown, D. C., et al., *BMC Immunology*, 2:9 (2001). Parallel plate flow chambers can be purchased from commercial suppliers such as GlycoTech (Gaithersburg, Md.).

Parallel plate flow chambers typically include two plates separated by a gasket. Fluid flows between the two plates. The gasket defines the height of the flow channel between the two plates and aids in channeling the direction of the flow of fluid. Biological cells are cultured on one of the glass slides which form the bottom of the chamber. The chamber is then sealed and a flow conditions are created that simulate in vivo flow conditions.

Parallel plate flow chambers can be used for stem cell and tissue engineering. Because certain factors required for cellular growth or response are only expressed and released when a fluid force is applied onto the cell, stem cells and tissue scaffolds grow better in a fluid flow environment rather than a static one.

A basic flow chamber includes (1) a base plate with an entrance and exit port through which cells and media are perfused, (2) a glass or plastic slide plate on which the substrate or cellular monolayer is placed, (3) a gasket that controls the chamber diameter, and (4) a vacuum outlet so that the apparatus can be held in place (Brown, D. C., et al., *BMC Immunology*, 2:9 (2001).

A syringe pump can be employed in the single pass configuration and a peristaltic pump can be used in the recirculating configuration. Internal tubing diameter can be the standard 0.062" ID as well as 0.02" ID and 0.01" ID tubing.

C. Cells

Cells used in the disclosed systems and methods are preferably mammalian, and most preferably human cells. Human umbilical vein endothelial cells or Chinese Hamster Ovary cells expressing human E- or P-selectin are typically used as the monolayer cells. The monolayer cells can express a cell adhesion molecule naturally. Alternatively, the monolayer cells can be genetically engineered to express one or more cell adhesion molecules of interest. The adhesion molecule that is expressed by the monolayer cells can be specific for a certain type of cell, for example stem cells, adult stem cells, induced pluripotent stem cells, mesenchymal stem cells, embryonic stem cells, and combinations thereof.

Cells of interested can then be perfused over the monolayer of cells and interactions between the monolayer and cells of interest can be observed. Basically any type of cells can be used. Preferred cells include, but are not limited to hematopoietic cell lines (such as HL60, KG1a, K562, THP-1), cancer cell lines (BT-20, MCF-7, MDA-MB-231, PC3, etc.) and stem cells (CD34+ hematopoietic stem/progenitor cells, hematopoietic stem cells derived from pluripotent progenitor cells, mesenchymal stem cells, to name a few.

D. Alexa Fluor® Dyes

The fluorescent probes that can be used in the disclosed systems and methods can be selected from those that are commercially available. For example several Alexa Fluor® Dyes can be purchased from Molecular Probes, Inc. and conjugated to secondary antibodies or other secondary binding moieties. Alternatively, secondary antibodies or other binding moieties conjugated to fluorophores can be purchased commercially.

TABLE 1

Exemplary Alexa Fluor ® Dyes that can be used.

| Dye | Color † | Absorb (nm) | Emit (nm) | MM (g/mol) | ε (cm$^{-1}$M$^{-1}$) | Quantum Yield |
|---|---|---|---|---|---|---|
| Alexa Fluor 350 | blue | 346 | 442 | 410 | 19,000 | — |
| 405 | violet | 401 | 421 | 1028 | 35,000 | — |
| 430 | green | 434 | 541 | 702 | 15,000 | Revival Based on Unavoidable Delay |
| 488 | cyan-green | 495 | 519 | 643 | 73,000 | 0.92 |
| 500 | green | 502 | 525 | 700 | 71,000 | — |
| 514 | green | 517 | 542 | 714 | 80,000 | — |
| 532 | green | 532 | 554 | 721 | 81,000 | 0.61 |
| 546 | yellow | 556 | 573 | 1079 | 112,000 | 0.79 |
| 555 | yellow-green | 555 | 565 | ~1250 | 155,000 | 0.1 |
| 568 | orange | 578 | 603 | 792 | 88,000 | 0.69 |
| 594 | orange-red | 590 | 617 | 820 | 92,000 | 0.66 |
| 610 | red | 612 | 628 | 1172 | 144,000 | — |
| 633 | Far-red | 632 | 647 | ~1200 | 159,000 | — |
| 635 | Far-red | 633 | 647 | — | 140,000 | — |
| 647 | Far-red | 650 | 665 | 1155.06[7] | 270,000 | 0.33 |
| 660 | Near-IR | 663 | 690 | ~1100 | 132,000 | 0.37 |
| 680 | Near-IR | 679 | 702 | ~1150 | 183,000 | 0.36 |
| 700 | Near-IR | 702 | 723 | ~1400 | 205,000 | 0.25 |
| 750 | Near-IR | 749 | 775 | ~1300 | 290,000 | 0.12 |
| 790 | Near-IR | 782 | 805 | — | 260,000 | — |

† = approximate color of the emission spectrum
ε = extinction coefficient

Additional fluorophores that can be used with the disclosed systems and methods, include but are not limited to those in Table 2.

TABLE 2

Additional Fluorophores

| Fluorophore | Absorption (nm) | Emission (nm) | Visible color |
|---|---|---|---|
| hydroxycoumarin | 325 | 386 | blue |
| methoxycoumarin | 360 | 410 | blue |
| aminocoumarin | 350 | 445 | blue |
| Cy2 | 490 | 510 | green (dark) |
| FAM | 495 | 516 | green (dark) |
| Fluorescein FITC | 495 | 518 | green (light) |
| HEX | 535 | 556 | green (light) |
| Cy3 | 550 | 570 | yellow |
| TRITC | 547 | 572 | yellow |
| R-phycoerythrin (PE) | 480 | 565 578 | yellow |
| Rhodamine Red | 570 | 590 | orange |
| Tamara | 565 | 580 | red |
| Cy3.5 | 581 | 596 | red |
| Rox | 575 | 602 | red |
| Allophycocyanin | 650 | 660 | red |
| Cy5 | 650 | 670 | red |
| Cy5.5 | 675 | 694 | red |
| TruRed | 490, 675 | 695 | red |
| Cy7 | 743 | 770 | red |
| Texas Red | 589 | 615 | red |

Antibodies, antigen binding fragments thereof, single chain antibodies, aptamers, can be labeled with one or more fluorophores. Typically, the antibodies labeled with the fluorophore specifically bind to other antibodies (primary antibodies). The primary antibodies can be specific for cell-specific antigens including extracellular proteins and peptides, carbohydrates, lipids, and combinations thereof.

III. The Fluorescent Multiplex Cell Flow (FMCF) Technique

One embodiment provides a multiple fluorescence staining approach, which allows at least eight different combinations of fluorescent cell identities to be run in a flow experiment at one time. For instance, each cell type or treatment condition can be labeled with a unique fluorescent identity, such as Alexa Fluor® 405-, Alexa Fluor® 546- or Alexa Fluor® 680-conjugated antibody or combinations thereof. Real-time images are then acquired in a single pass using line-scanning spectral confocal microscope at one frame per 400-millisecond rate. This technique allows for the analysis of adhesion events from up to eight different treatment conditions simultaneously in real-time and to calculate differences in rolling frequency, velocity and tethering capability of cells under study. This assay allows for analysis of rolling cell populations on an endothelial cell layer where populations are competing for occupancy of available sites of interactions in a real-time scenario much like what occurs in vivo.

Treatments can be developed that direct the migration of therapeutic cells, such as stem cells, to specific locations throughout the body but also to inhibit metastasis of detrimental cells such as circulating tumor cells.

Using such assays to measure the rolling process for candidate cell types may lead to development of techniques to enhance cell homing and contribute significantly towards improving cell-based therapy or techniques to inhibit tumor spreading and cancer mortality. Importantly, this technology described here allows for multiple conditions to be tested with improved throughput, permitting rapid and efficient study of rolling properties. Other assays relevant for cell homing, such as cell adhesion, chemotaxis and transmigration may also be studied with this assay. Overall, this high throughput approach to following the flow of cells over a endothelial monolayer emerges as a powerful technique to study cell rolling and will become a useful tool to aid in the clinical translation of exogenous cell-based therapies.

One embodiment provides staining multiple cell specimens with the same or different primary antibody or other primary binding agent. The primary binding agent specifically binds to an epitope on the cell specimen. The binding agent can be an antibody, epitope binding fragment of the antibody, an aptamer, fusion protein, or a combination thereof. The cell specimen is then treated with a secondary binding agent that specifically binds to the primary binding agent. The secondary binding agent can be an antibody, epitope binding fragment of the antibody, an aptamer, fusion protein, or a combination thereof, that is labeled with a detectable label. In a preferred embodiment, the detectable label is a fluorophore. Each cell specimen is treated with a second binding agent that is labeled with a unique detectable label. In one embodiment, the detectable labels are Alexa Fluor® 405-, Alexa Fluor® 546- or Alexa Fluor® 680. It is understood that the fluorophores are selected so that the excitation laser lines do not intersect.

Once the cell specimens are treated or contacted with the secondary binding agent, the cell specimens are optionally washed to remove any non-specific binding of the binding agents, for example the secondary binding agent. After the optional washing step, the cell specimens are added system 100. In one embodiment, the parallel plate flow chamber has a bottom layer that is covered with a monolayer of cells, for example endothelial cells. The monolayer of cells expresses naturally or is engineered to express a cell adhesion molecule. The cell specimens are perfused through the parallel plate flow chamber and exposed to an amount of electromagnetic radiation to excite the fluorophores conjugated to the second binding agent. Real-time images are taken as the cell specimens perfuse through the parallel plate flow chamber and fluorescence micrograph images are displayed on a computer. In one embodiment, simultaneous excitation is achieved using three laser lines (488 nm, 561 nm, and 633 nm). Typically the cell specimens are used at a concentration of $1\times10^6$/ml to $1\times10^2$/ml. The range of shear stress in the parallel plate flow chamber can be in the range of 0.5-5 dynes/cm$^2$. In some embodiments, the shear stress can be 6, 7, 8, 9, 10, 11, 12, 13, 14, 15, 16, 17, 18, 19, or 20 dynes/cm$^2$.

The cells in the cell specimens can be adult tissue cells, stem cells, induced pluripotent stem cells, embryonic stem cells, or any other mammalian cell. Preferably, the cells are human cells. Before or during the assay, test compounds can be added to the cells to investigate the effect the test compound may have on the adhesion of the cell specimens to the monolayer.

EXAMPLES

Example 1: Fluorescent Multiplex Cell Flow System

FIG. 1 shows a parallel plate flow chamber set-up used to capture adhesive events between flowing cells and endothelial cells in real time with some modifications. This apparatus is used to visualize tethering and rolling (mediated by the selectins and their ligands) and firm adhesion (mediated by integrins and chemokines) of flowing cells on substrate-expressing cells (i.e., endothelial cells). This embodiment includes a suspension of flowing cells connected via soft tubing of the flow chamber inlet line to the parallel plate flow chamber. Flowing cells are moving over a monolayer of substrate-expressing cells under fixed sheer stress brought up by controlling the flow rate using a syringe pump in addition to the thickness of flow chamber rubber gasket. The flow experiment is imaged using a spectral confocal laser scanning system connected to a computer.

Example 2: Fluorescent Multiplex Cell Flow Technique

Figure 2A:
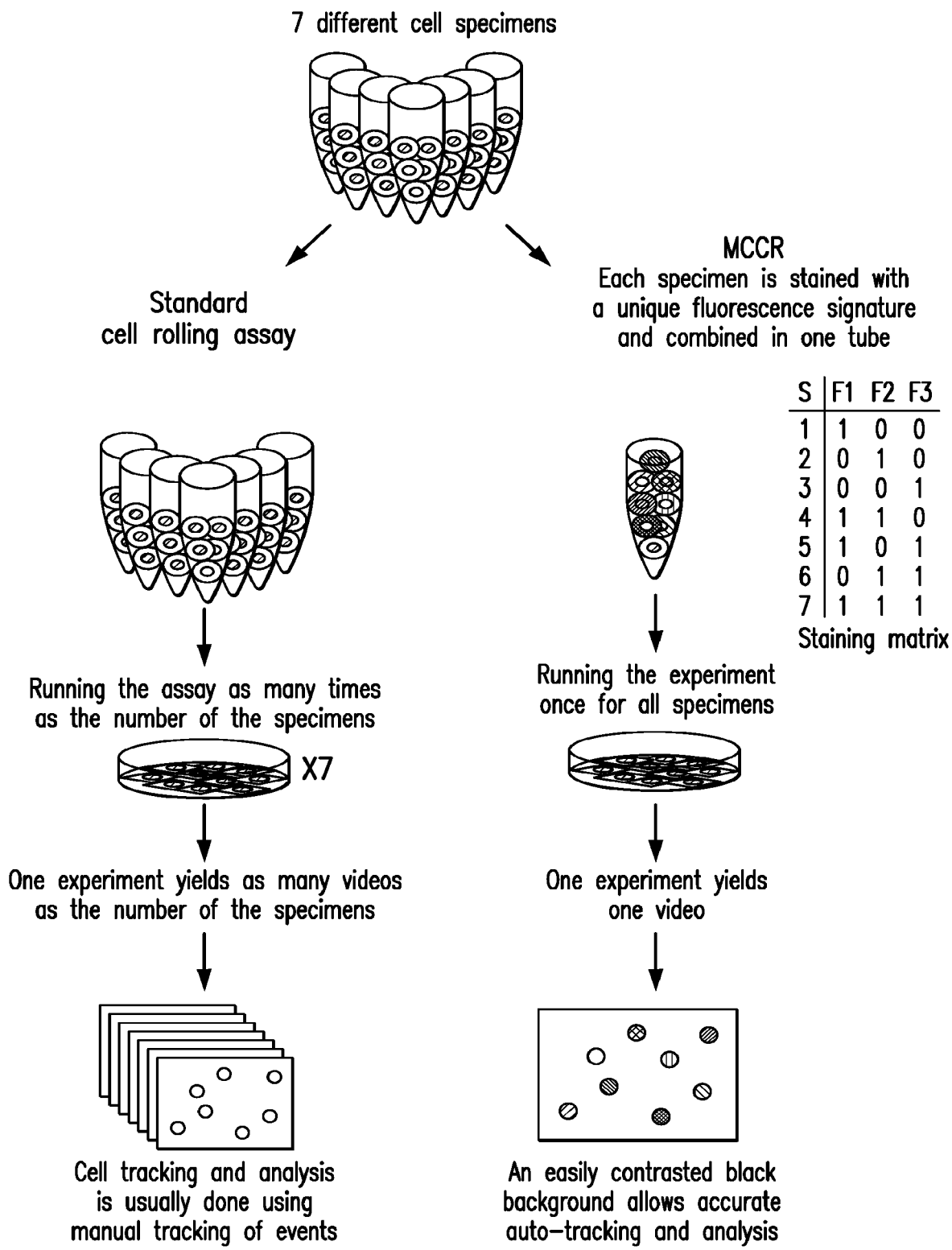
FIG. 2A is a diagram depicting the comparison of the Fluorescent Multiplex Cell Flow technique (right side) to the standard light microscope-based cell rolling technique (left side).
Figure 2B:
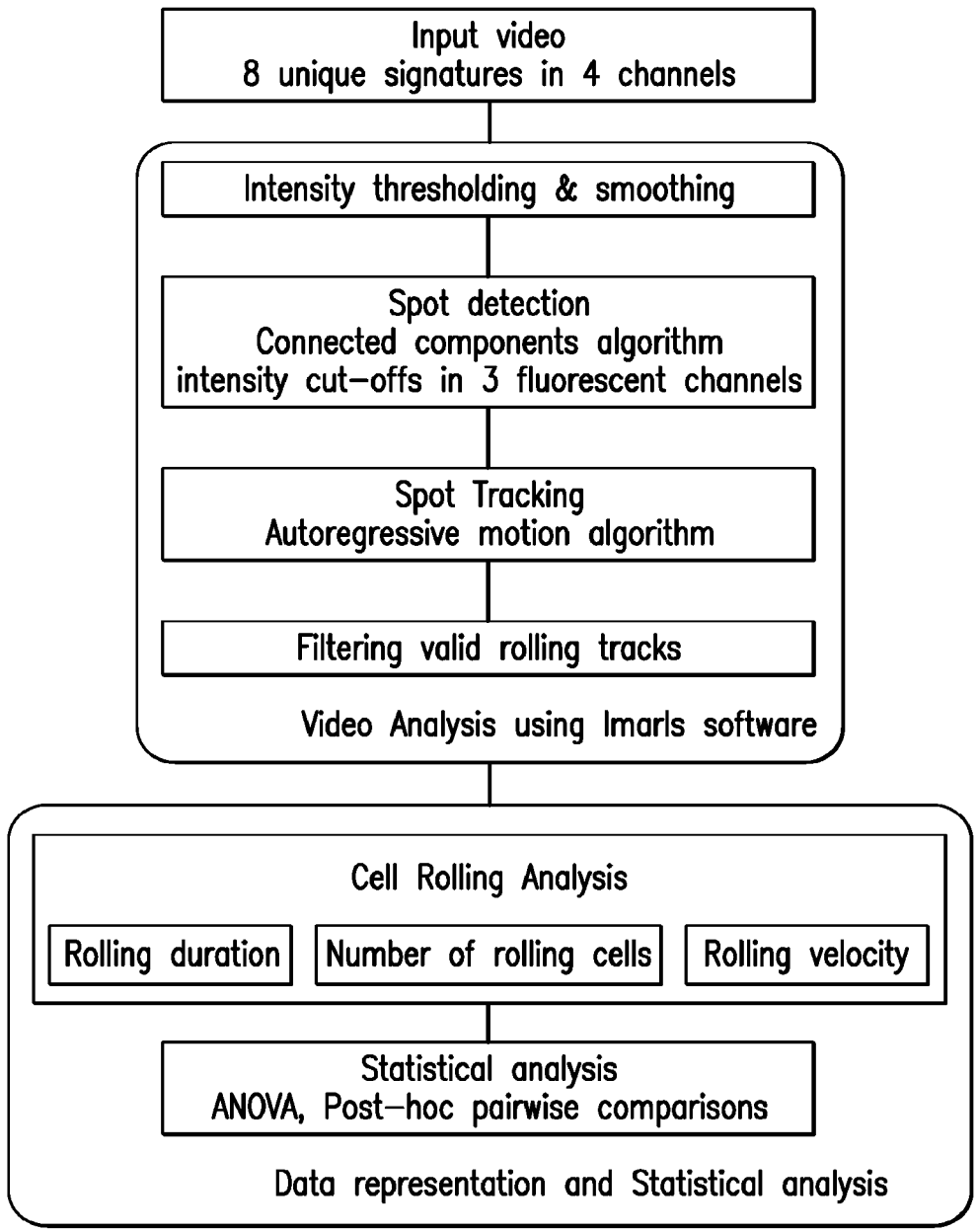
FIG. 2B is a schematic of the analysis pipeline.
Figure 2C:
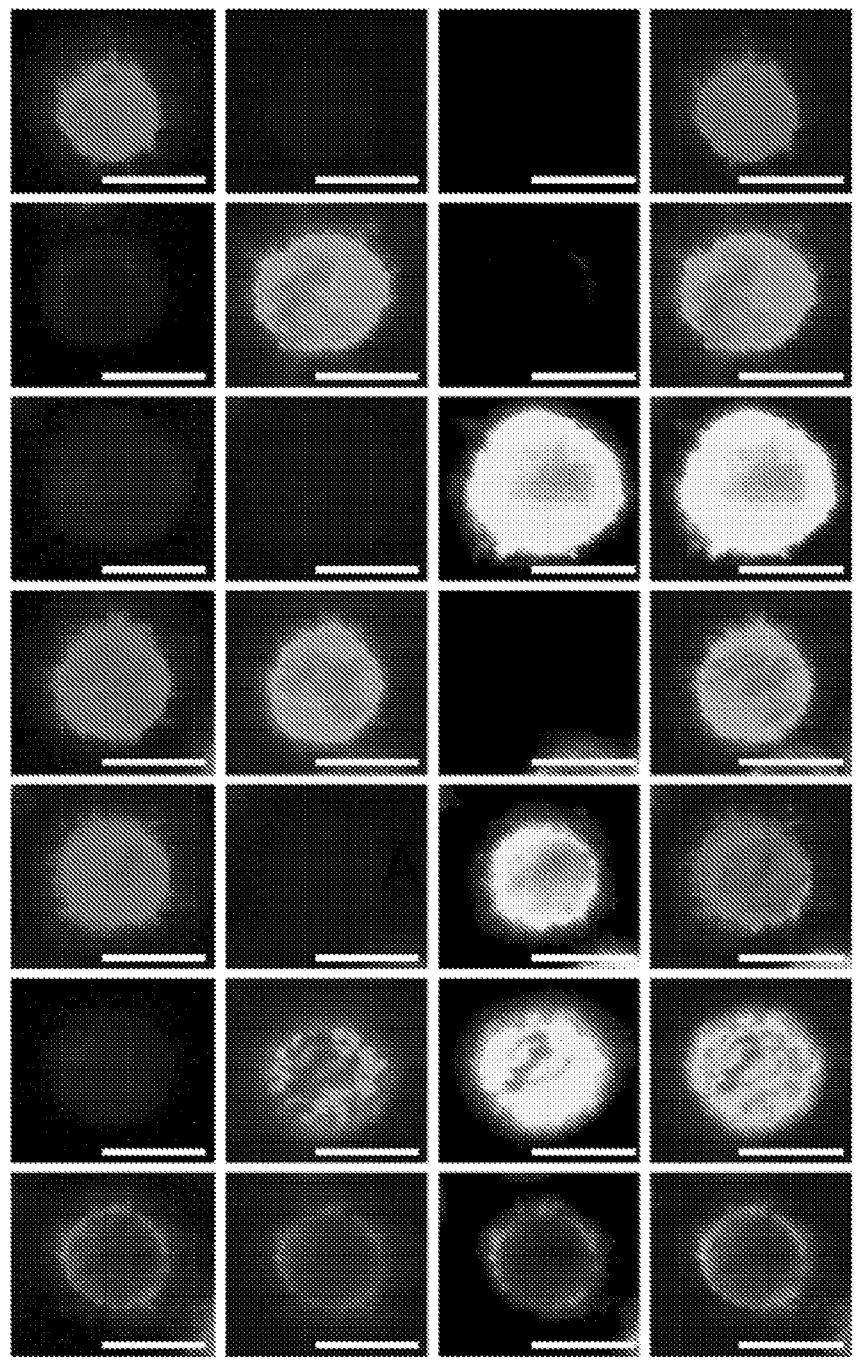
FIG. 2C shows a panel of fluorescent micrographs in grey scale. The columns from left to right show fluorescence of cells stained with secondary antibodies conjugated to Alexa Fluor 405, Alexa Fluor 564, or Alexa Fluor 680. The last column shows a combination of the preceding three columns.
Figure 2D:
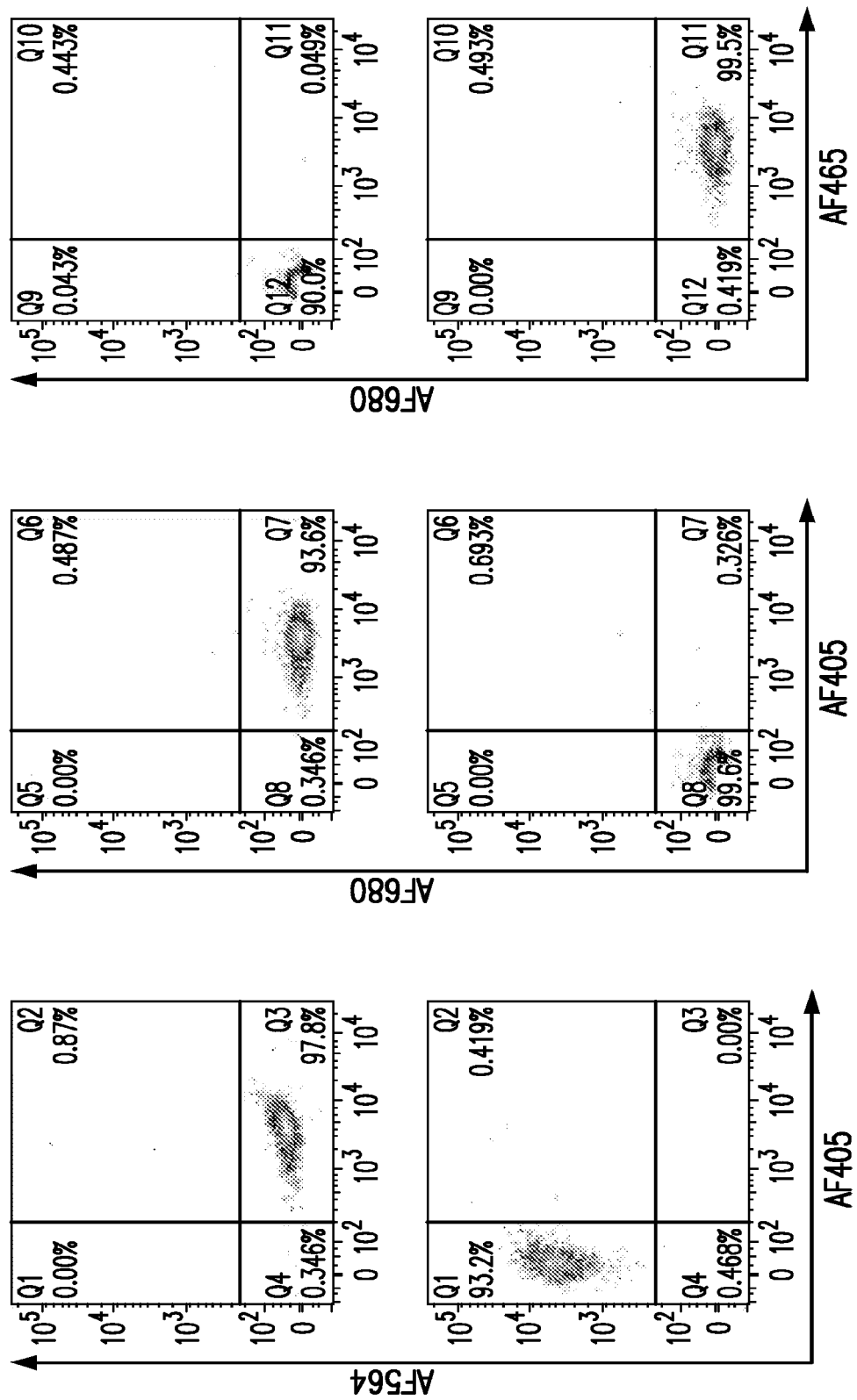
FIG. 2D shows the flow cytometric analysis for uncompensated data showed acceptably low or no spectral overlap in detection channels.
Figure 2D:
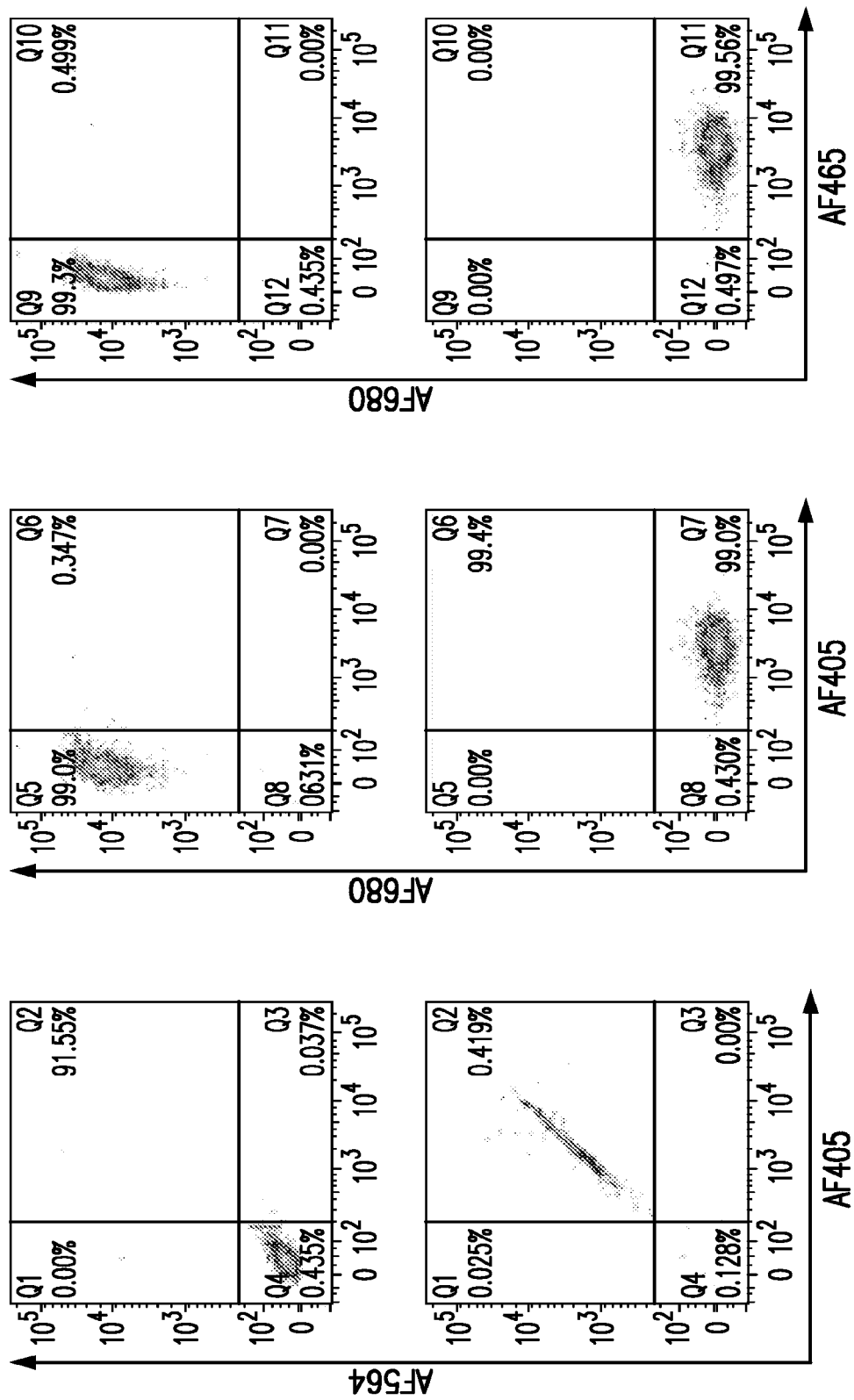
Figure 2D:
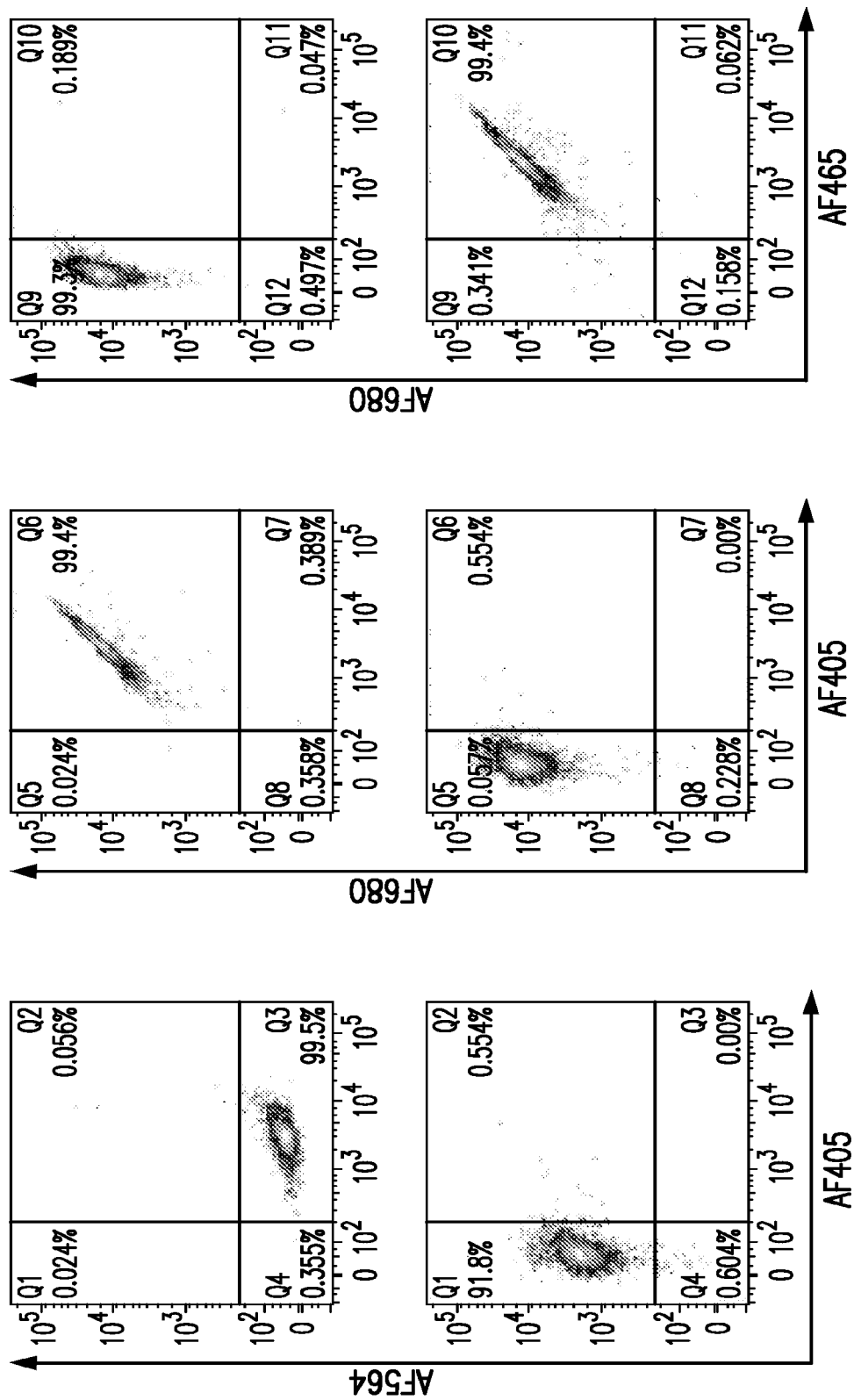
Figure 2D:
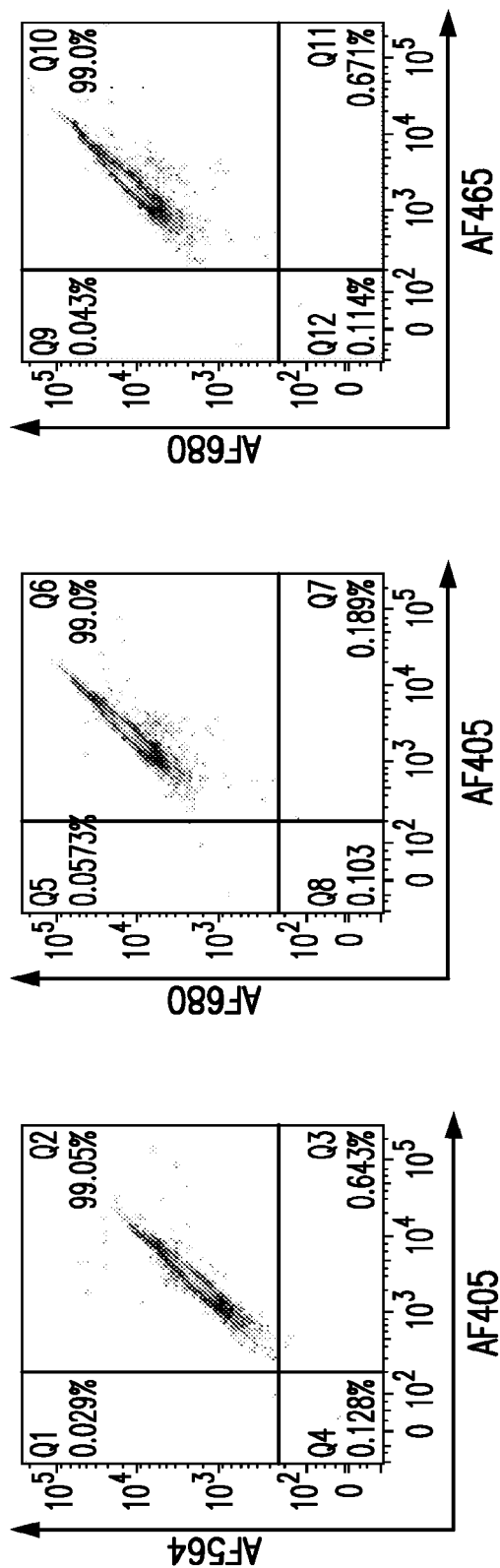
Figure 2E:
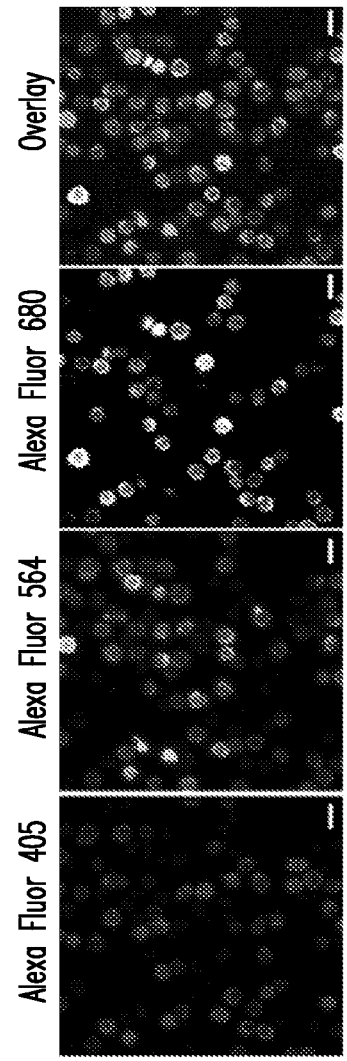
FIG. 2E shows examples of confocal images of a mixture of seven specimens uniquely labeled with seven different color signatures detected using simultaneous excitation using three laser lines (488 nm, 561 nm and 633 nm) and detected in three intervals with no intersection with excitation laser lines. A video of seven-color frames is the raw input for downstream rolling analysis, cell detection and tracking. Size bar=20 μm.
Figure 3A:
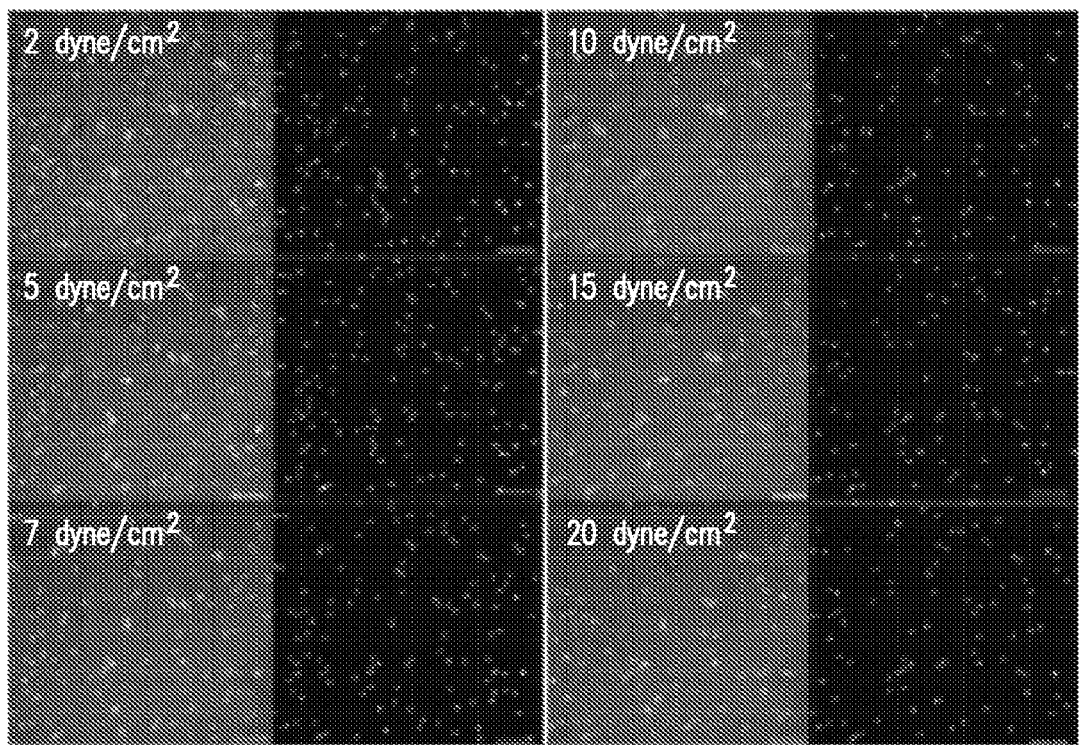
FIG. 3A is a panel of fluorescence micrographs of 8 KG-1a cell samples.
Figure 3B:
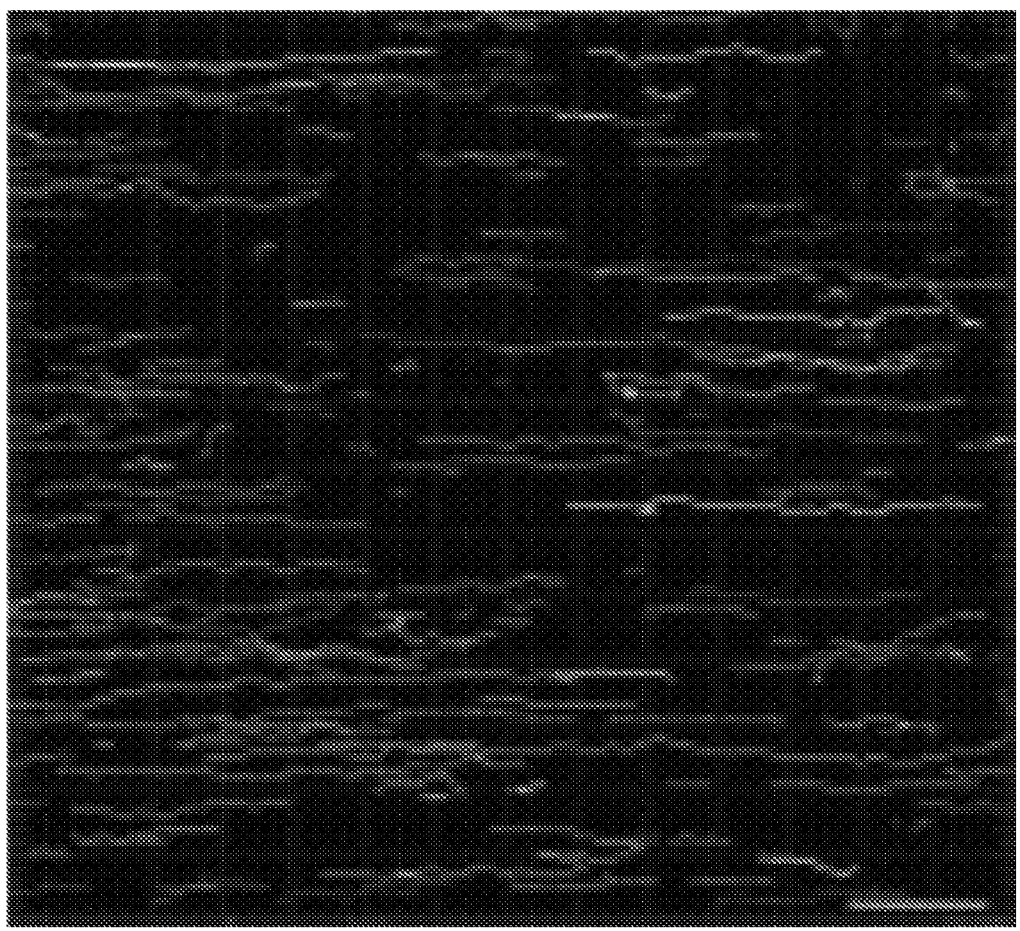
FIG. 3B is a panel of fluorescence micrographs showing cell rolling of 8 KG-1a cell samples.
Figure 3C:
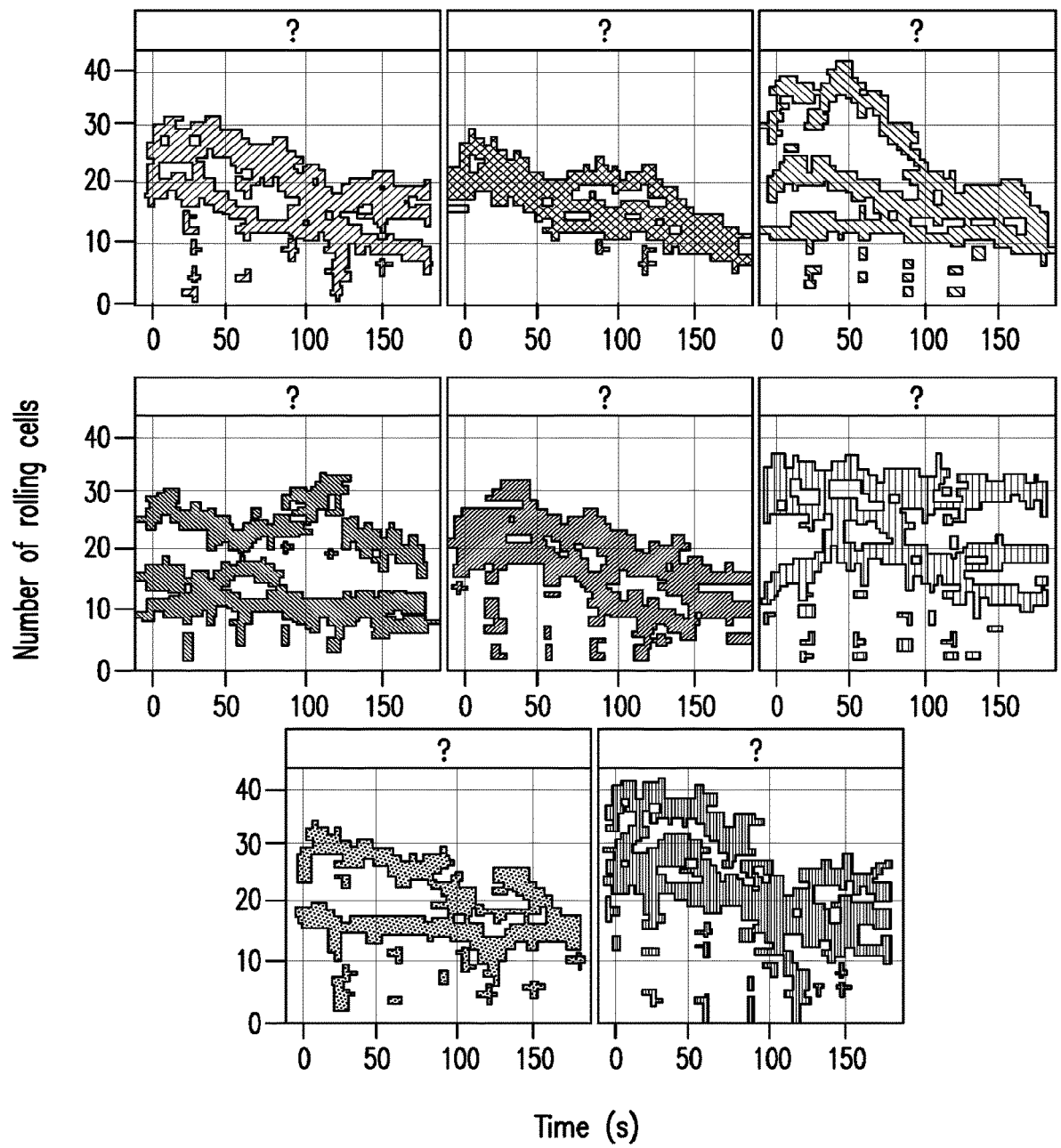
FIG. 3C is a panel of line graphs of number or rolling cells versus time (secs) for KG-1a cell samples.
Figure 3D:
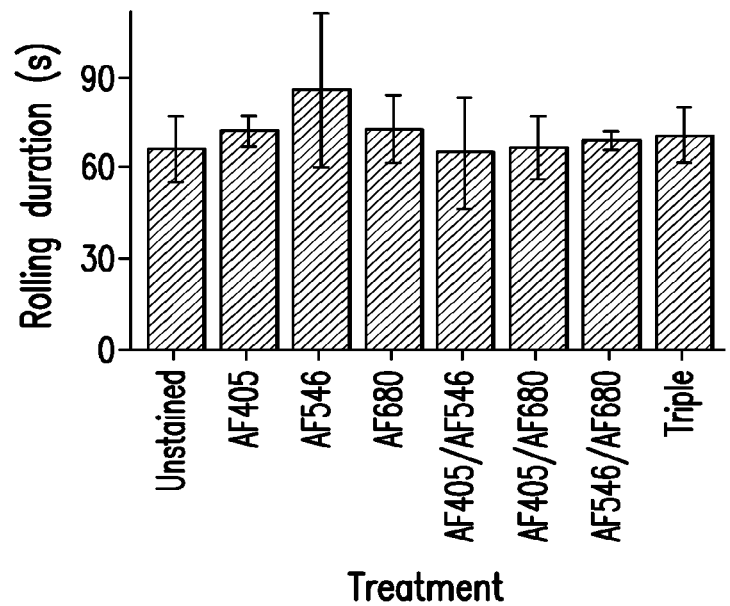
FIG. 3D is a bar graph of rolling duration (s) for unstained cells and cells stained with the following: AF 405, 546, 680, 405/546. 405/680, 546/680, and Triple.
Figure 3E:
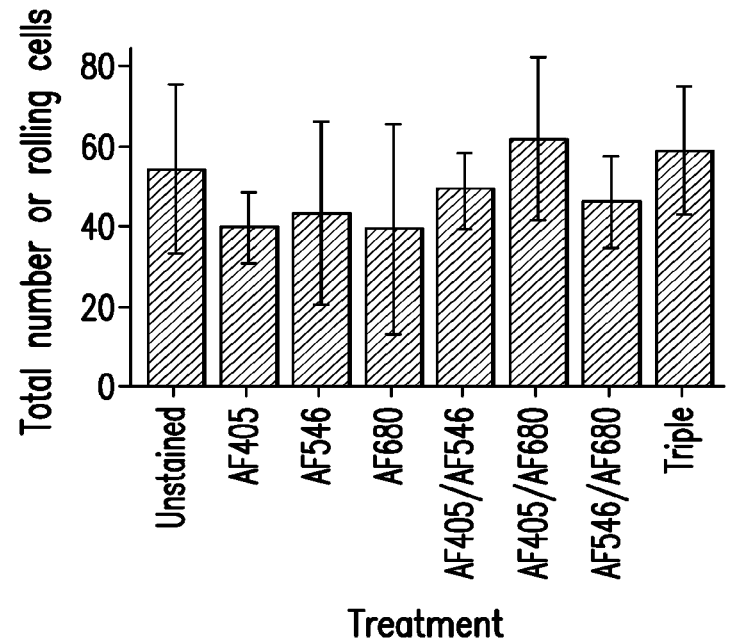
FIG. 3E is a bar graph of total number of rolling cells for cells stained with the following AF 405, 546, 680, 405/546. 405/680, 546/680, and Triple.
Figure 3F:
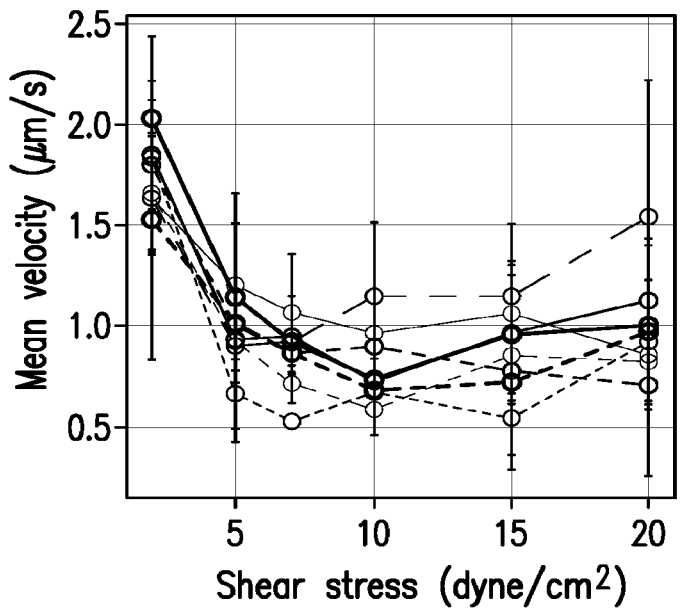
FIG. 3F is a line graph of mean velocity (μm/sec) versus shear stress (dynes/cm$^2$) for cells stained with the following AF 405, 546, 680, 405/546. 405/680, 546/680, and Triple.
Figure 3G:
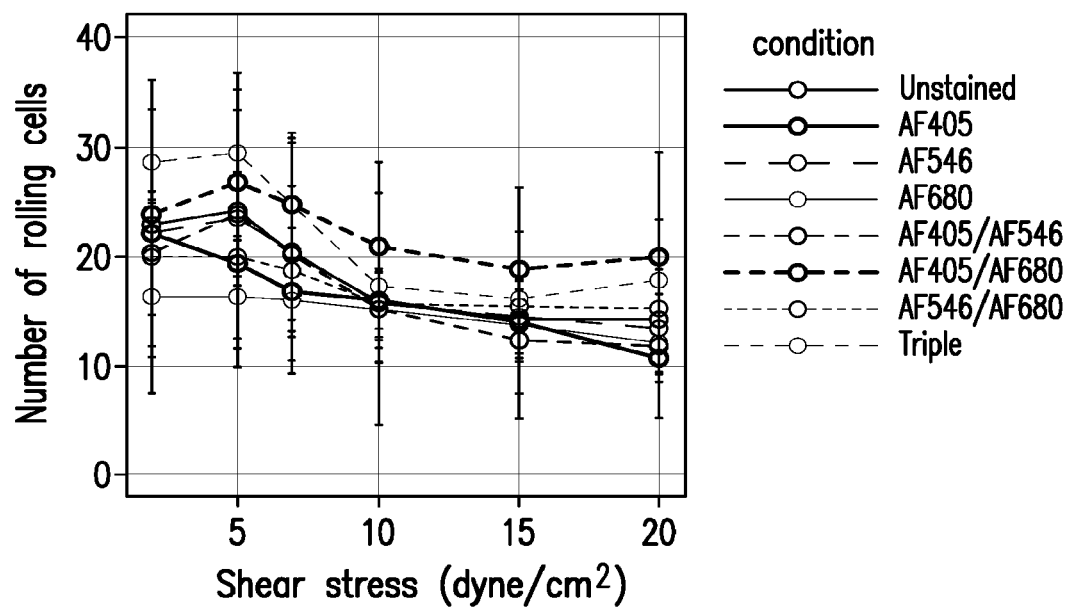
FIG. 3G is a line graph of number of rolling cells versus shear stress (dynes/cm$^2$) for cells stained with the following AF 405, 546, 680, 405/546. 405/680, 546/680, and Triple. The data show that dye loading does not influence cell rolling.
Figure 4A:
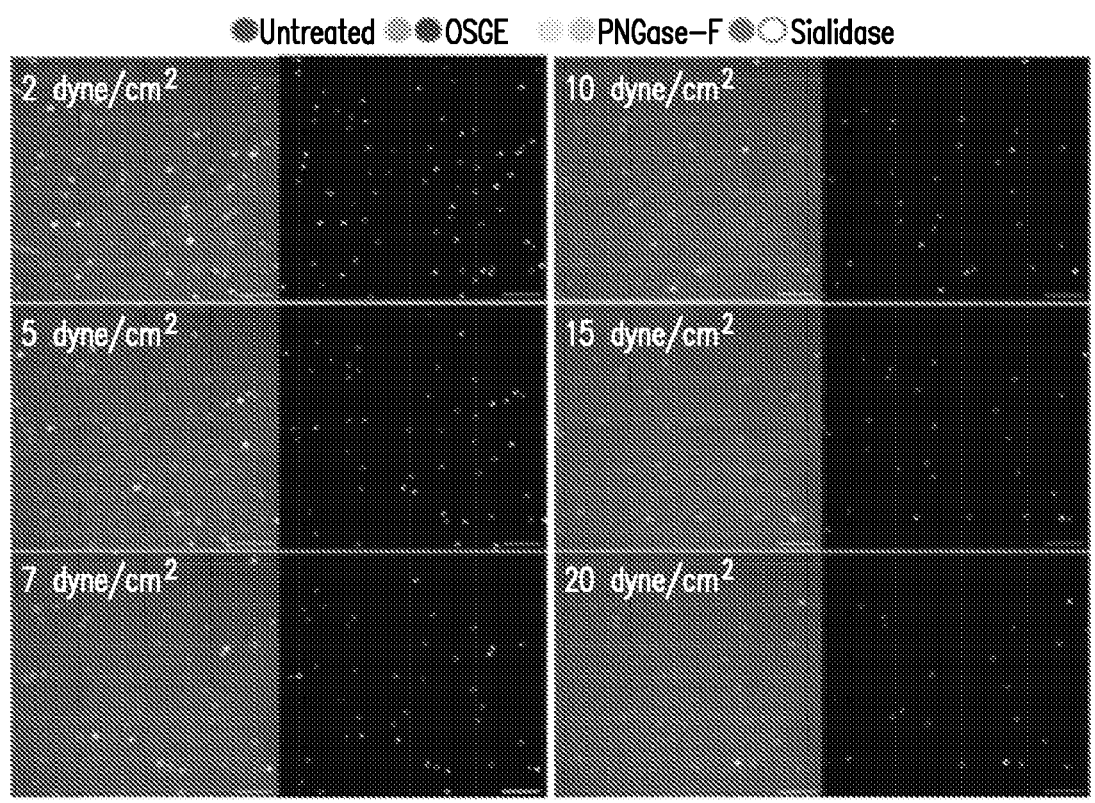
FIG. 4A and FIG. 4B are fluorescence micrographs showing impairment of cell rolling of KG-1a cells after glycosidase treatment. Bar=100 μm.
Figure 4B:
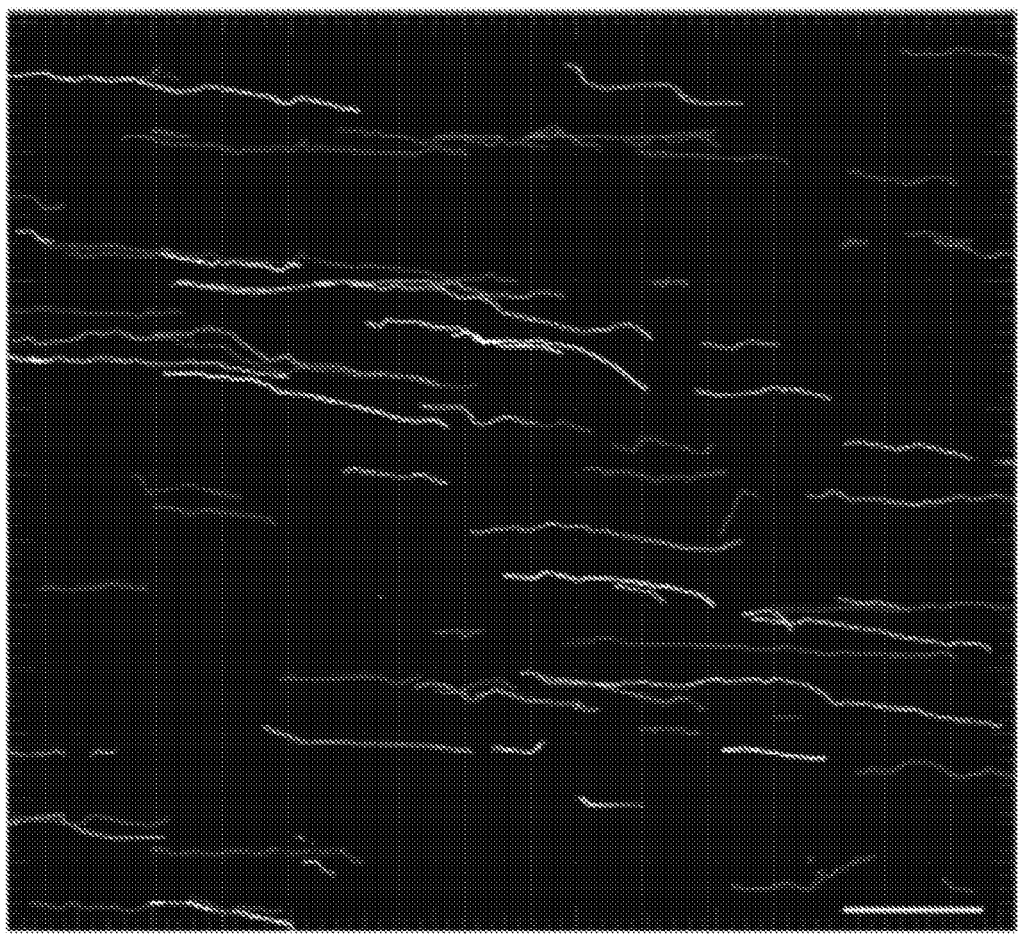
Figure 4C:
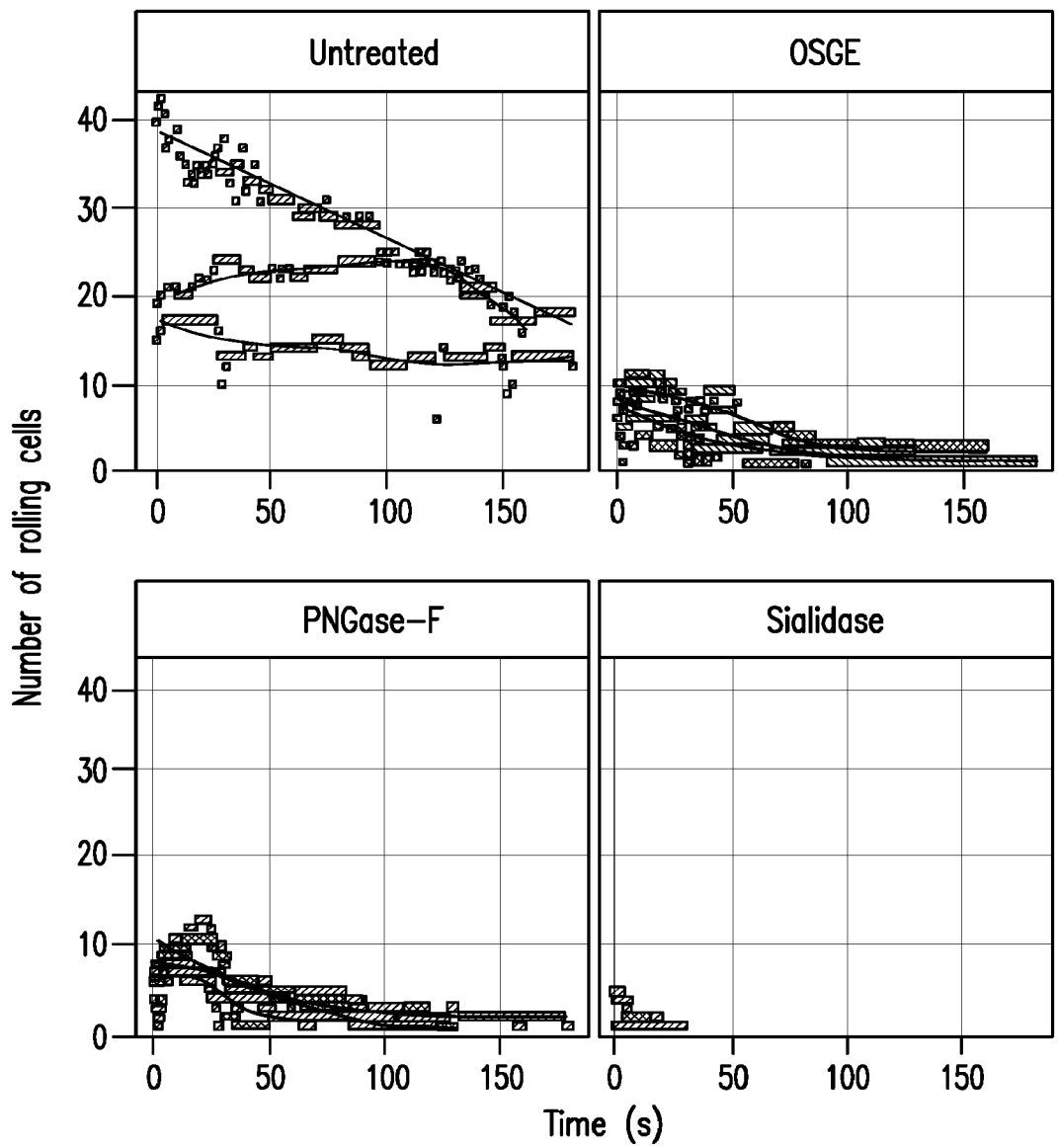
FIG. 4C is a panel of line graphs of number of rolling cells versus time for untreated, OSGE, PNGase-F, and sialidase.
Figure 4D:
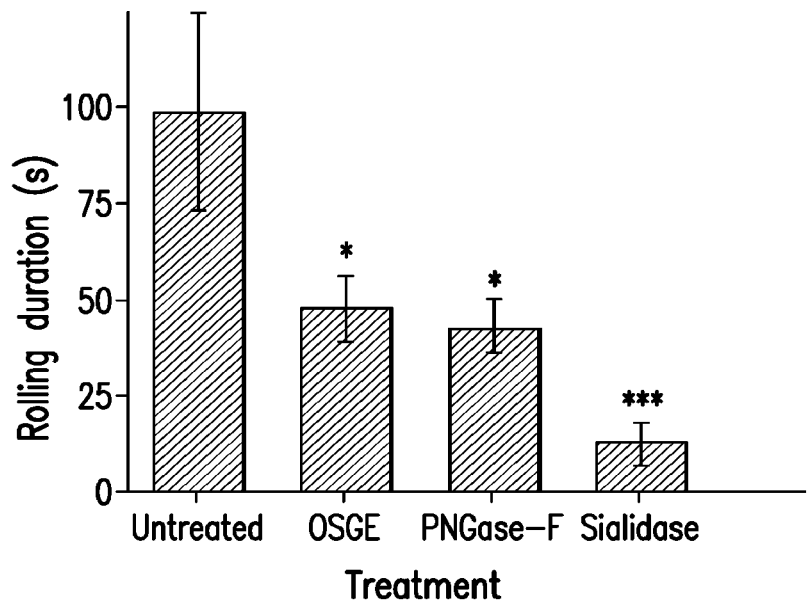
FIG. 4D is bar graph of rolling duration (secs) for untreated cells and cells treated with the following: OSGE, PNGase-F, and Sialidase.
Figure 4E:
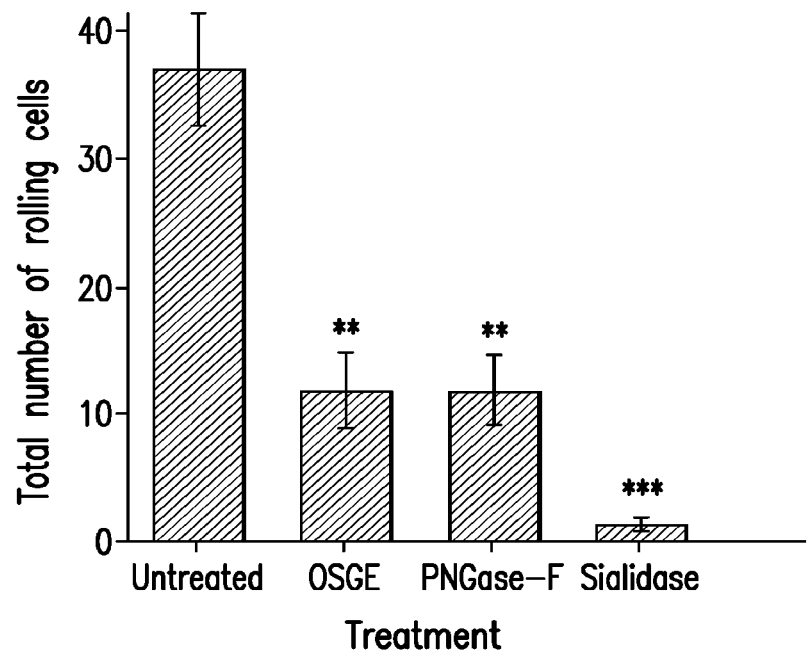
FIG. 4E is a bar graph of total number of rolling cells for untreated cells, and cells treated with the following: OSGE, PNGase-F, and Sialidase.
Figure 4F:
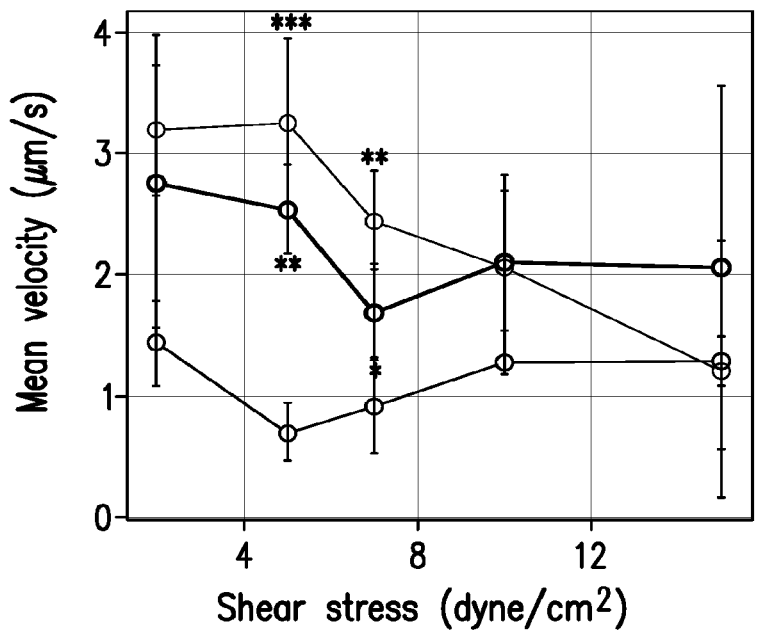
FIG. 4F is a line graph of mean velocity (μm/sec) versus shear stress (dynes/cm$^2$) for untreated cells, and cells treated with the following: OSGE, PNGase-F, and Sialidase.
Figure 4G:
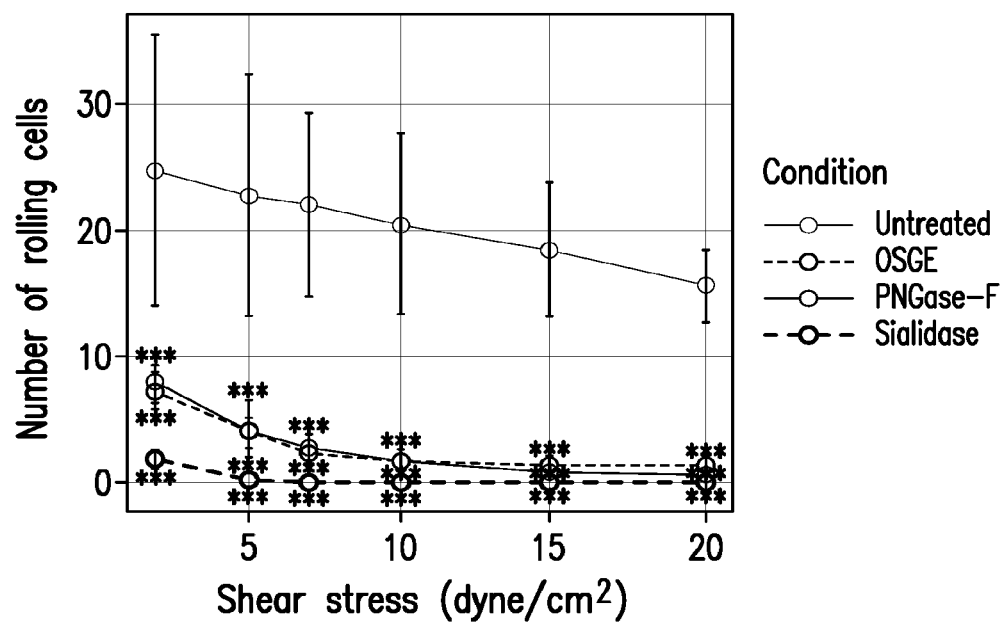
FIG. 4G is a line graph of number of rolling cells versus shear stress (dynes/cm$^2$) for untreated cells, and cells treated with the following: OSGE, PNGase-F, and Sialidase.
Figure 5A:
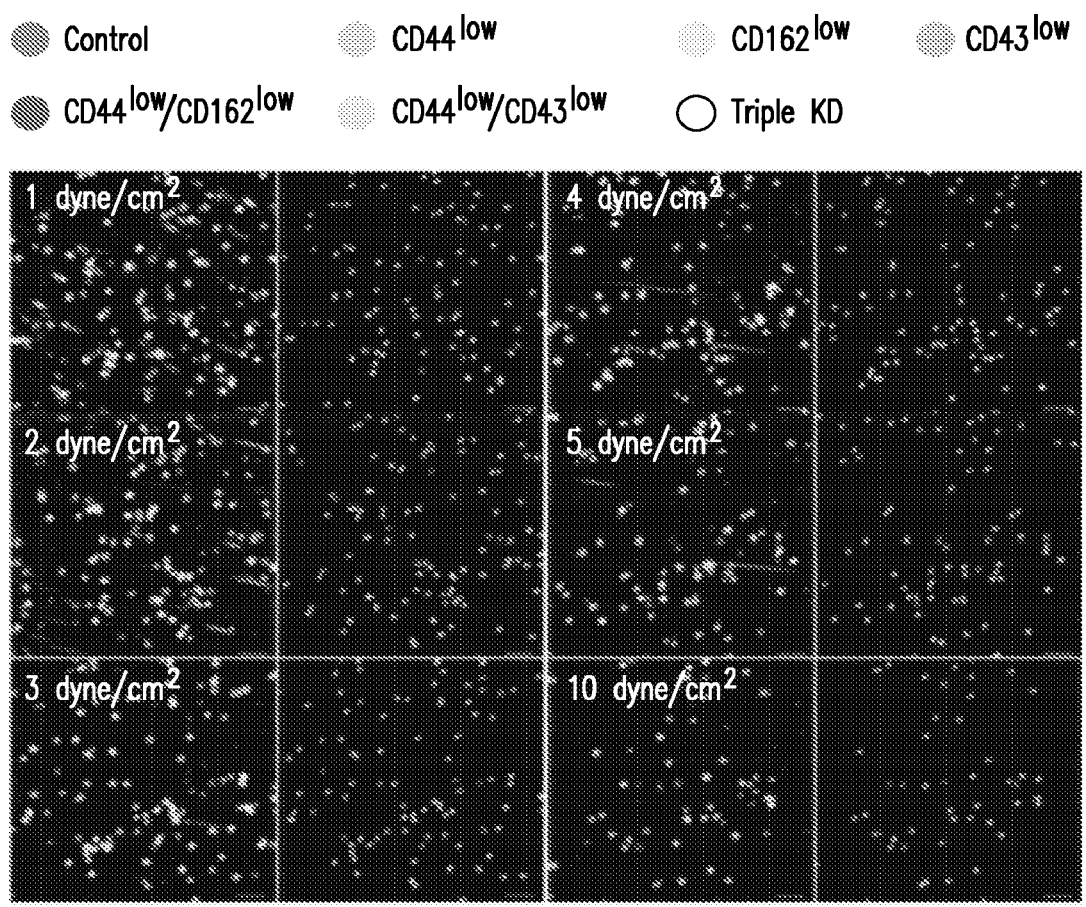
FIG. 5A and FIG. 5B are fluorescence micrographs showing knock down of T cells.
Figure 5B:
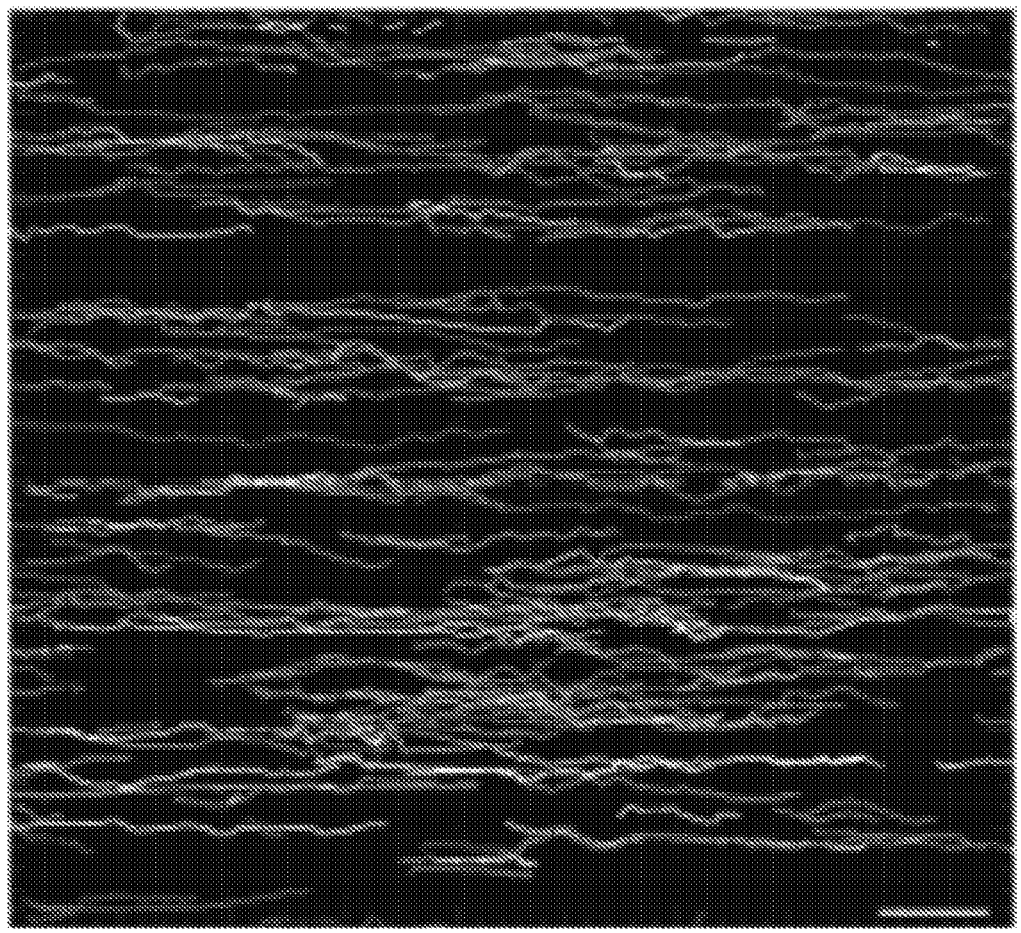
Figure 5C:
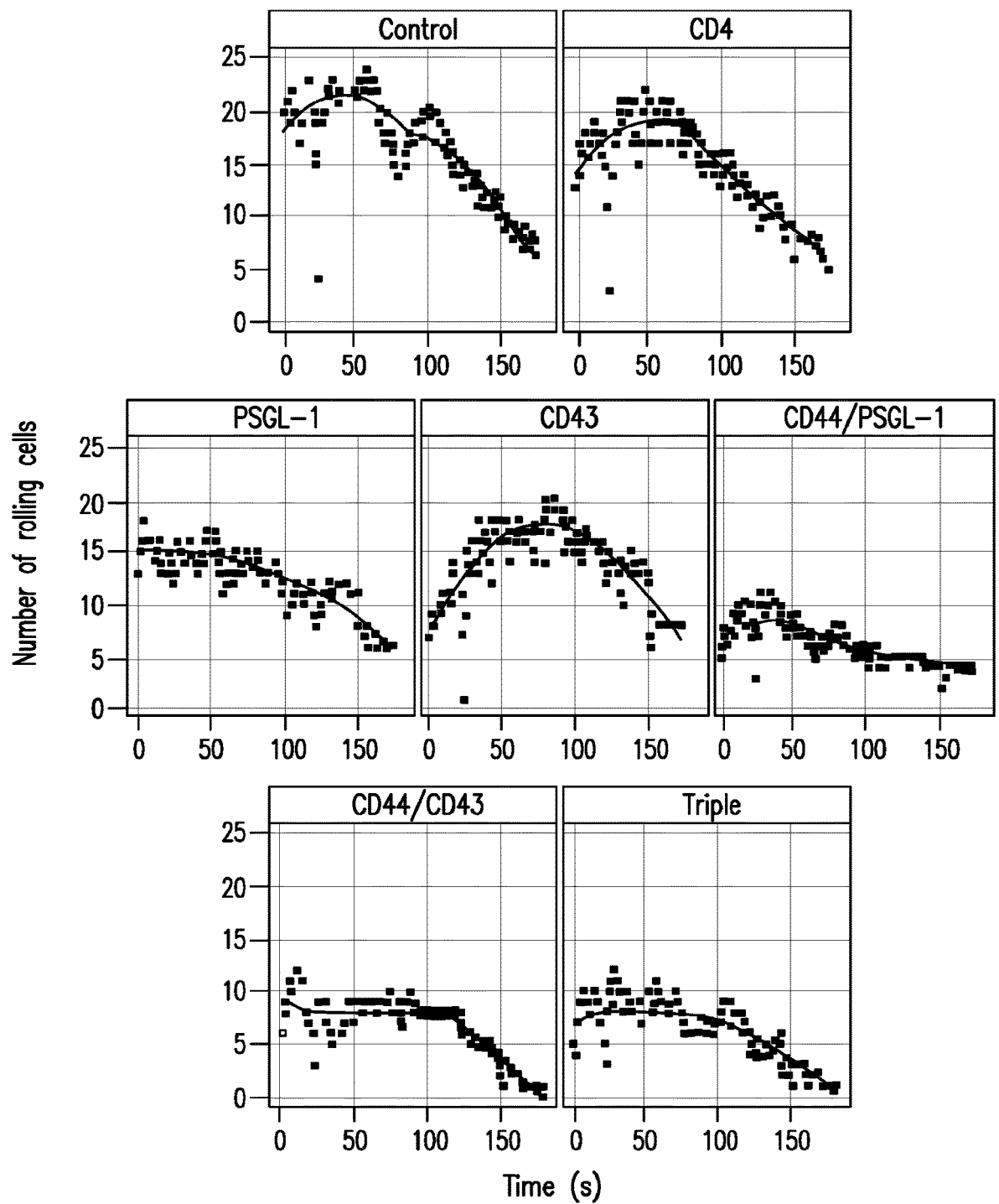
FIG. 5C shows a panel of line graphs of number of rolling cells versus time (secs).
Figure 5D:
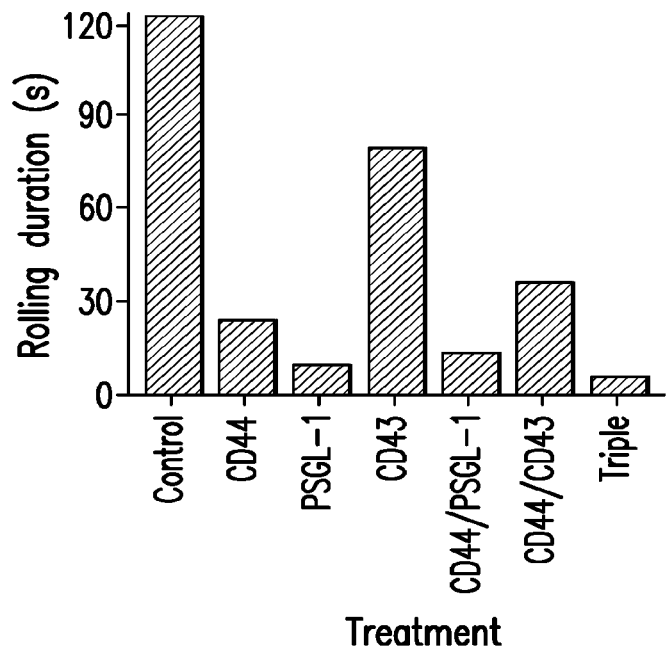
FIG. 5D is a bar graph of rolling duration (s) for control cells, and cells treated with CD4, PSGL-1, CD43, CD44/PSGL-1, CD44/CD43 and triple.
Figure 5E:
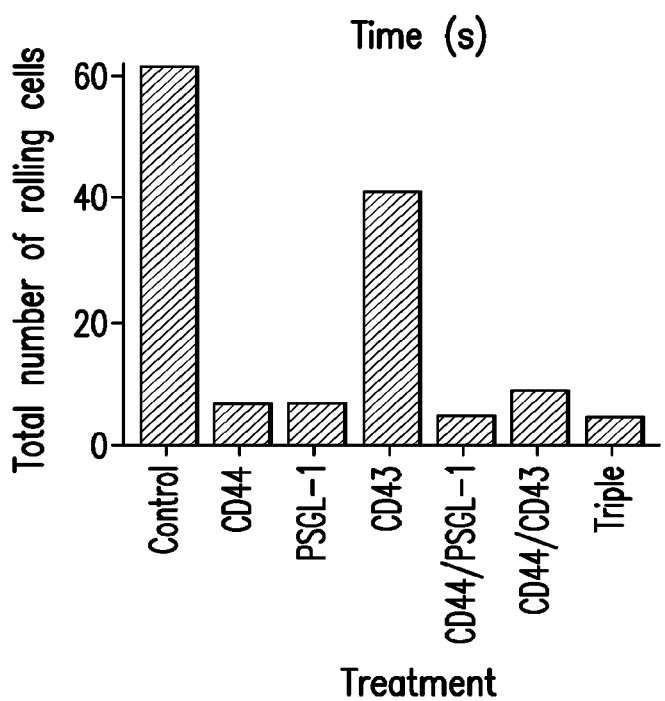
FIG. 5E is a bar graph of total number of rolling cells for control cells and cells treated with CD4, PSGL-1, CD43, CD44/PSGL-1, CD44/CD43 and triple.
Figure 5F:
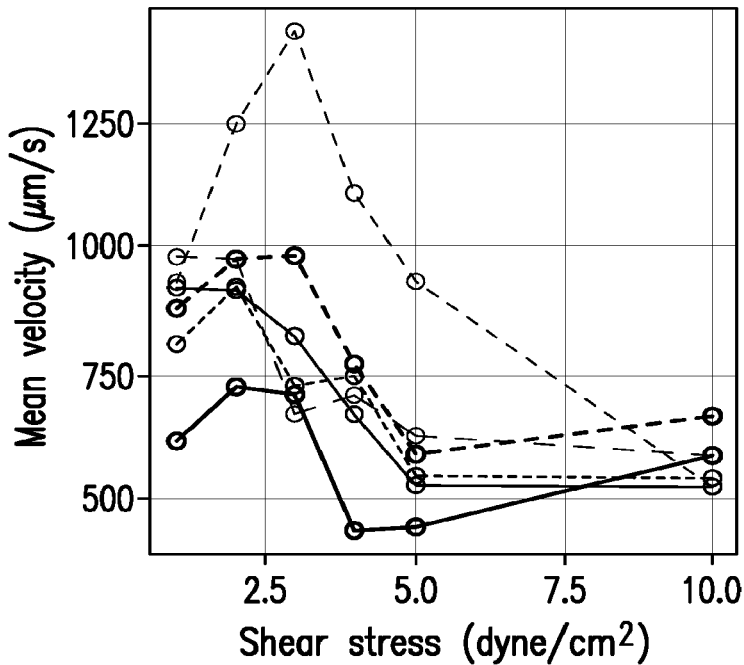
FIG. 5F is a line graph of mean velocity (μm/sec) versus shear stress (dynes/cm$^2$) for control cells and cells treated with CD4, PSGL-1, CD43, CD44/PSGL-1, CD44/CD43 and triple.
Figure 5G:
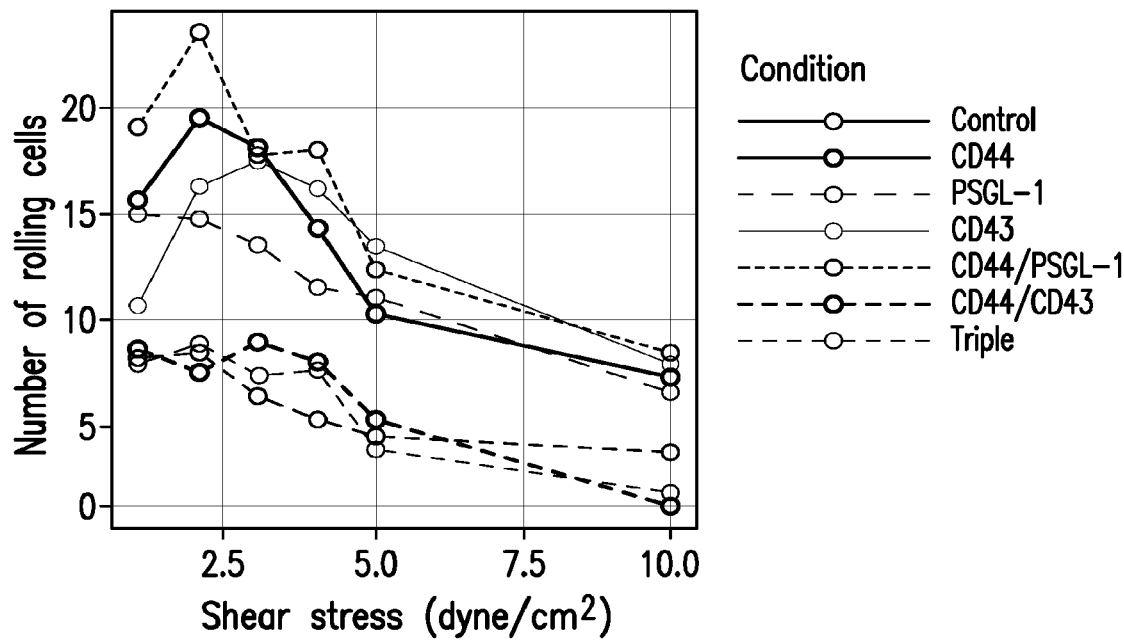
FIG. 5G is a line graph of number or rolling cells versus shear stress (dynes/cm$^2$) for control cells and cells treated with CD4, PSGL-1, CD43, CD44/PSGL-1, CD44/CD43 and triple.

FIG. 2A shows a diagram depicting the comparison of an exemplary Fluorescent Multiplex Cell Flow (FMCF) technique (right side) to the standard light microscope-based cell rolling technique (left side). FIG. 2B shows efficient labeling of seven samples in the FMCF technique using a combination of 3 differently labeled secondary antibodies. Live cells from each specimen/condition were stained with the same primary antibody followed by staining with secondary antibodies conjugated to Alexa Fluor 405 (blue), Alexa Fluor 546 (green) or Alexa Fluor 680 (red) or combinations thereof. Size bar=10 µm. FIG. 2C shows seven unique signatures were confirmed. Flow cytometric analysis for uncompensated data showed acceptably low or no spectral overlap in detection channels. FIG. 2D shows examples of confocal images of a mixture of seven specimens uniquely labeled with seven different colour signatures detected using simultaneous excitation using three laser lines (488 nm, 561 nm and 633 nm) and detected in three intervals with no intersection with excitation laser lines. A video of seven-color frames is the raw input for downstream rolling analysis, cell detection and tracking. Size bar=20 µm.

The data show it was possible to color-code up to 8 samples using a combination of 3 fluorophore-conjugated secondary antibodies. Spectral overlap was ruled out using confocal fluorescence imaging and FACS analysis. Using fluorescence multiplexing with identical samples showed statistically uniform rolling parameters. Fluorescence multiplexing was successfully used to confirm reproducibility with internal replication. Removing glycans and sialic acid significantly reduced rolling parameters of cells in flow. CD44 and PSGL-1 have a decisive role in controlling the rolling of human activated T cells over E-selectin expressing cells.

While in the foregoing specification this invention has been described in relation to certain embodiments thereof, and many details have been put forth for the purpose of illustration, it will be apparent to those skilled in the art that the invention is susceptible to additional embodiments and that certain of the details described herein can be varied considerably without departing from the basic principles of the invention.

All references cited herein are incorporated by reference in their entirety. The present invention may be embodied in other specific forms without departing from the spirit or essential attributes thereof and, accordingly, reference should be made to the appended claims, rather than to the foregoing specification, as indicating the scope of the invention.

We claim:

1. A method for assaying cell adhesion or cell rolling of multiple cell specimens comprising:
   (a) contacting each cell specimen with a primary binding agent that specifically binds to an epitope on the surface of cells in the cell specimen;
   (b) contacting each cell specimen with a second binding agent conjugated to a fluorescent label, wherein each cell specimen is contacted with a second binding agent comprising a different fluorescent label and the second binding agent specifically binds to the primary agent bound to an epitope on the surface of cells in the cell specimen;
   (c) perfusing the cell specimens contacted with the second binding agents through a parallel plate flow chamber comprising a monolayer of cells;
   (d) exciting the fluorescent labels with an amount of electromagnetic energy; and
   (e) capturing real-time fluorescence images of the multiple cell specimens as the multiple cell specimens pass through the parallel plate flow chamber.

2. The method of claim 1, wherein the cell specimens comprise mammalian cells.

3. The method of claim 2, wherein the mammalian cells comprise human cells.

4. The method of claim 1, wherein the cell specimens comprise stem cells.

5. The method of claim 4, wherein the stem cells are selected from the group consisting of adult stem cells, embryonic stem cells, and induced pluripotent stem cells.

6. The method of claim 1, wherein the parallel plate flow chamber comprises a monolayer of cells.

7. The method of claim 6, wherein the monolayer of cells comprises endothelial cells.

8. A method for assaying cell adhesion or cell rolling of multiple cell specimens comprising:
   (a) contacting each cell specimen with a primary binding agent that specifically binds to an epitope on the surface of cells in the cell specimen;
   (b) contacting each cell specimen with a second binding agent conjugated to a fluorescent label, wherein each cell specimen is contacted with a second binding agent comprising a different fluorescent label and the second binding agent specifically binds to the primary agent bound to an epitope on the surface of cells in the cell specimen;
   (c) perfusing the cell specimens contacted with the second binding agents through a parallel plate flow chamber comprising a monolayer of endothelial cells;
   (d) exciting the fluorescent label with an amount of electromagnetic energy; and
   (e) capturing real-time fluorescence images of the multiple cell specimens as the multiple cell specimens pass through the parallel plate flow chamber, wherein the monolayer of cells are genetically engineered to express an epitope specifically bound by cells in the cell specimens.

9. The method of claim 8, wherein the cell specimens comprise mammalian cells.

10. The method of claim 9, wherein the mammalian cells comprise human cells.

11. The method of claim 8, wherein the cell specimens comprise stem cells.

12. The method of claim 11, wherein the stem cells are selected from the group consisting of adult stem cells, embryonic stem cells, and induced pluripotent stem cells.

* * * * *